United States Patent
Yamamoto et al.

(10) Patent No.: US 6,780,976 B2
(45) Date of Patent: Aug. 24, 2004

(54) ENONE REDUCTASES, METHODS FOR PRODUCING SAME, AND METHODS FOR SELECTIVELY REDUCING A CARBON-CARBON DOUBLE BOND OF AN ALPHA,BETA-UNSATURATED KETONE USING THE REDUCTASES

(75) Inventors: Hiroaki Yamamoto, Ibaraki (JP); Norihiro Kimoto, Ibaraki (JP)

(73) Assignee: Daicel Chemical Industries, Ltd., Osaka (JP)

( * ) Notice: Subject to any disclaimer, the term of this patent is extended or adjusted under 35 U.S.C. 154(b) by 0 days.

(21) Appl. No.: 10/081,644

(22) Filed: Feb. 21, 2002

(65) Prior Publication Data

US 2002/0192782 A1 Dec. 19, 2002

(30) Foreign Application Priority Data

Feb. 23, 2001 (JP) .................................... 2001-049363

(51) Int. Cl.[7] ......................... C07K 14/00; C12N 9/00
(52) U.S. Cl. ...................................... 530/350; 435/183
(58) Field of Search .......................... 568/315, 347; 435/6, 69.1, 183, 189, 94.1, 252.3, 320.1, 254.1, 254.2, 254.21; 530/300, 350; 536/23.1, 23.3, 23.7, 23.74

(56) References Cited

PUBLICATIONS

Wells, Biochemistry, vol. 29 No. 37, pp. 8509–8517 (1990).*
Bowie et al., Science, vol. 247, pp. 1306–1310 (1990).*
Kawai et al., "Asymmetric Reduction of α,β–Unsaturated Ketones with a Carbon–Carbon Double–Bond Reductase from Baker's Yeast", Tetrahedron Letters, 39:5225–5228, 1998.
Kitamura et al., "Purification of NADPH–Linked α,β–Ketoalkene Double Bond Reductase from Rat Liver", Arch. Biochem. Biophys., 282:183–187, 1990.
Shimoda et al., "Stereochemistry in the Reduction of Enones by the Reductase from *Euglena gracilis* Z", Phytochem. 49:49–53, 1998.
Shimoda et al., "Biotransformation of enones with biocatalysts—two enone reductases rom *Astasia longa*", J. mol. Catalysis B: Enzymatic, 8:255–264, 2000.
Wanner et al., "Purification and characterization of two enone reductases from *Saccharomyes cerevisiae*", Eur. J. Biochem., 225:275–278, 1998.
Mallet et al., A 43.5 kb Segment of Yeast Chromosome XIV, which contains *MFA2, MEP2, CAP/SRV2, NAM9, FKB1/FPR1/RBP1, MOM22* and *CPT1*, Predicts an Adenosine Deaminase Gene and 14 New Open Reading Frames, Yeast, 11(12) 1195–209, 1995.
EMBL Accession No. Z46843 (Jun. 1, 1995).
EMBL Accession No. Z71410 (May 6, 1996).
EMBL Accession No. U22383 (Apr. 1, 1995).
EMBL Accession No. X59720 (Mar. 16, 1992.
SWISS–PROT Accession No. P53912 (Oct. 1, 1996).
SWISS–PROT Accession No. P25608 (May 1, 1992).

* cited by examiner

*Primary Examiner*—Jeffrey Stucker
*Assistant Examiner*—Zachariah Lucas
(74) *Attorney, Agent, or Firm*—Fish & Richardson P.C.

(57) ABSTRACT

The object of the present invention is to provide novel enone reductases useful for producing ketones. Accordingly, novel enone reductases derived from the genus Kluyveromyces are provided by the present invention. In addition, the present invention also provides genes encoding the enzymes and vectors containing the genes, as well as transformants. Furthermore, the present invention provides enone reductases derived from yeast. Methods for selectively reducing the carbon-carbon double bonds of α,β-unsaturated ketones using these enone reductases are provided. Ketones useful as a raw material for pharmaceuticals can be produced based on an enzymatic reaction.

6 Claims, 3 Drawing Sheets

ENONE REDUCTASES, METHODS FOR PRODUCING SAME, AND METHODS FOR SELECTIVELY REDUCING A CARBON-CARBON DOUBLE BOND OF AN ALPHA,BETA-UNSATURATED KETONE USING THE REDUCTASES

TECHNICAL FIELD

The present invention relates to novel enone reductases which are useful for reducing an α,β-unsaturated bond of an α,β-unsaturated ketone (enone), and polynucleotides encoding such reductases, as well as methods for producing the reductases and methods for selectively reducing a carbon-carbon double bond of an α,β-unsaturated ketone using the reductases or a polypeptide having homology with the enzyme.

BACKGROUND

Ketones are compounds that are widely used as raw materials in the synthesis of organic compounds. In addition, ketones are also important raw materials for the production of optically active alcohols and optically active amines that are optically active intermediates important in the synthesis of pharmaceuticals. For example, α,β-unsaturated ketones obtainable by the condensation reaction of aldehydes and ketones are useful as precursors for these ketones.

For example, 3-methyl-3-penten-2-one can be readily prepared by the condensation of acetaldehyde and 2-butane (J. Amer. Chem. Soc., 81:1117–1119, 1959).

Various ketones can be obtained by selectively reducing the α,β-unsaturated bonds of α,β-unsaturated carbonyl compounds. Hydrogenation reactions using Ni catalyst or Pd-C catalyst ("Catalytic Hydrogenation Reaction" p135, Tokyo Kagaku Dojin (1987)) are methods known in the art for selectively reducing the α,β-unsaturated bonds alone, without reducing any carbonyl groups. However, these methods have the following problems to be solved: (1) carbonyl groups may be also reduced by continuing the reaction; (2) metals, which have adverse effects on the environment, are used as the catalysts; and (3) high-pressure hydrogen gas is required for the reaction. Importantly, the reduction of carbonyl groups leads to decrease of the ketone yield.

On the other hand, methods using organisms as follows are reported as methods for selectively reducing carbon-carbon double bonds of α,βunsaturated ketones using biological reactions:

plant cells (J. Nat. Prod. 56:1406–1409, 1993);
baker's yeast (Tetrahedron Lett. 52:5197–5200, 1978; Bull. Chem. Soc. Jpn. 64:3473–3475, 1991; Tetrahedron Asym. 6:2143–2144, 1995; etc.); and
fungus (J. Org. Chem. 47:792–798, 1982).

However, these biological methods have their own problems such as: (1) carbonyl groups are also reduced; (2) low reactivity; and (3) cell preparation on a large-scale is difficult. Further, various types of enone reductases derived from these organisms have been reported. However, genes encoding these reductases remain to be cloned, and it is therefore hard to conveniently prepare these enzymes on a large scale.

In addition to the above-mentioned reductases of the α,β-unsaturated carbonyl compounds, such reductases as follows have been reported. These reductases are not suitable for industrial applications because either the substrate specificity of these reductases remains to be clarified or the selectivity for the α,β-unsaturated bond is low.

Clostridium tyrobutyricum-derived 2-enoate reductase (E.C.1.3.1.31) (J. Biotechnol. 6:13–29, 1987);
Clostridium kluyveri-derived acryloyl-CoA reductase (Biol. Chem. Hoppe-Seyler 366:953–961, 1985);
Enone reductase YER-2 purified from baker's yeast (Kawai et al. ((Kyoto University), The $4^{th}$ Biocatalyst symposium, Abstract p58 (2001));
Enone reductases purified from a baker's yeast EI and EII (Eur. J. Biochem. 255:271–278, 1998);
Enone reductase (verbenone reductase; also referred to as p90) derived from tobacco (Nicotiana tabacum) cells (J. Chem. Soc., Chem. Commun. 1426–1427, 1993; Chem. Lett. 850–851, 2000);
Carvone reductase (also referred to as enone reductase-I), which is an enone reductase derived from tobacco (Nicotiana tabacum) cells (Phytochemistry 31:2599–2603, 1992):
Enone reductase-II, p44, and p74, which are enone reductases derived from tobacco (Nicotiana tabacum) cells;
Enone reductases purified from Euglena gracilis and Astasia longa, which are plant species (Phytochemistry 49, 49–53 (1998)); and
Enone reductase purified from rat liver (Arch. Biochem. Biophys. 282:183–187, 1990).

SUMMARY

The object of the present invention is to provide novel enone reductases, which have an enzyme activity to selectively reduce the α,β-unsaturated bonds of α,β-unsaturated ketones to produce α,β-saturated ketones, and genes encoding the reductases. Another object of the present invention is to provide methods for selectively reducing the carbon-carbon double bonds of α,β-unsaturated ketones using the reductases and organisms producing the reductases.

The present inventors screened enzymes producing 2-butanone from methyl vinyl ketone and found that Kluyveromyces lactis has the activity of interest. Then, they purified the enzyme having the activity of interest from fungal cells of Kluyveromyces lactis, and revealed the properties thereof. They confirmed that the enzyme selectively reduced the α,β-unsaturated bonds of α,β-unsaturated ketones in a β-nicotinamide adenine dinucleotide phosphate (NADPH)-dependent manner, and that the enzyme has substantially no activity to reduce ketones. Further, the present inventors cloned a gene encoding the enzyme, clarified the structure thereof, and verified that the gene was novel. In addition, they overexpressed the gene in a heterologous organism to obtain a transformed strain having higher selectivity and higher activity at the same time to reduce the α,β-unsaturated bonds of α,β-unsaturated ketones in a NADPH-dependent manner. Furthermore, they found that selective reduction of the carbon-carbon double bonds of α,β-unsaturated ketones can be achieved by the enzyme, homologues thereof, cells producing them, and so on, and thus, completed the present invention. Hereinafter, β-nicotinamide adenine dinucleotide phosphate is referred to as NADP; β-nicotinamide adenine dinucleotide as NAD; and the reduced forms thereof as NADPH and NADH, respectively.

More specifically, the present invention relates to the following enone reductases, polynucleotides encoding the reductases, methods for producing the reductases, and methods for selectively reducing carbon-carbon double bonds of α,β-unsaturated ketones using the reductases or polypeptides having homology to such reductases.

[1] An enone reductase having the following physicochemical properties:
(A) Action:
   The enzyme reduces the carbon-carbon double bonds of the α,β-unsaturated ketones, using NADPH as an electron donor, to produce the corresponding saturated hydrocarbon;
(B) Substrate specificity:
   The details of one or more embodiments of the invention are set forth in the accompanying drawings and the description below. Other features, objects, and advantages of the invention will be apparent from the description and drawings, and from the claims.
   (1) the enzyme reduces the carbon-carbon double bonds of the α,β-unsaturated ketones but has substantially no activity to reduce ketones;
   (2) the enzyme exhibits a significantly higher activity with NADPH than with NADH as the electron donor;
   (3) the enzyme does not substantially act on substrates, wherein both substituents at the β carbon relative to the ketone are not hydrogen; and
   (4) the enzyme does not substantially act on substrates, wherein the carbon-carbon double bond is present in the cyclic structure; and
(C) Optimal pH:
   pH 6.5–7.0;
[2] The enone reductase of [1], wherein the reductase further has the following physicochemical properties:
(D) Optimum temperature:
   37–45° C.
(E) Molecular weight:
   The molecular weight of the reductase determined by sodium dodecyl sulfate-polyacrylamide gel electrophoresis and by gel filtration is about 43,000 and about 42,000, respectively;
[3] The novel enone reductase of [1], which is derived from the genus Kluyveromyces;
[4] A method for obtaining the enone reductase of [1], comprising the step of culturing a microorganism belonging to the genus Kluyveromyces and having the ability of producing to the novel enone reductase of [1];
[5] The method of [4], wherein the microorganism belonging to the genus Kluyveromyces is *Kluyveromyces lactis*;
[6] A polynucleotide encoding a polypeptide having enone-reducing activity selected from the group of:
(a) a polynucleotide comprising the nucleotide sequence of SEQ ID NO:1;
(b) a polynucleotide encoding the amino acid sequence of SEQ ID NO:2;
(c) a polynucleotide encoding a polypeptide comprising the the amino acid sequence of SEQ ID NO:2, in which one or more amino acids are substituted, deleted, inserted, and/or added;
(d) a polynucleotide hybridizing under stringent conditions with a polynucleotide consisting of the nucleotide sequence of SEQ ID NO:1; and
(e) a polynucleotide encoding an amino acid sequence exhibiting 60% or higher percent identity to the amino acid sequence of SEQ ID NO:2;
[7] A polypeptide encoded by the polynucleotide of [6];
[8] A recombinant vector comprising the polynucleotide of [6];
[9] The recombinant vector of [8], wherein a polynucleotide encoding a dehydrogenase catalyzing oxidation-reduction reactions using NADP as a coenzyme is further inserted;
[10] A transformant harboring the polynucleotide of [6] or the vector of [8] in an expressible manner;
[11] A method for producing the polypeptide of [7], comprising the step of culturing the transformant of [10];
[12] A polynucleotide encoding a polypeptide having enone-reducing activity selected from the group of:
(a) a polynucleotide comprising the nucleotide sequence of any one of SEQ ID NO:3, SEQ ID NO:5, and SEQ ID NO:7;
(b) a polynucleotide encoding a polypeptide comprising the amino acid sequence of any one of SEQ ID NO:4, SEQ ID NO:6, and SEQ ID NO:8.
(c) a polynucleotide encoding the amino acid sequence comprising the sequence of any one of SEQ ID NO:4, SEQ ID NO:6, and SEQ ID NO:8, in which one or more amino acids are substituted, deleted, inserted and/or added;
(d) a polynucleotide hybridizing under stringent conditions with a polynucleotide consisting of the nucleotide sequence of any one of SEQ ID NO:3, SEQ ID NO:5, and SEQ ID NO:7; and
(e) a polynucleotide encoding an amino acid sequence exhibiting 60% or higher percent identity to the amino acid sequence of any one of SEQ ID NO:4, SEQ ID NO:6, and SEQ ID NO:8;
[13] A polypeptide encoded by the polynucleotide of [12];
[14] A recombinant vector wherein the polynucleotide of [12] has been inserted;
[15] The recombinant vector of [14], wherein a polynucleotide encoding a dehydrogenase catalyzing oxidation-reduction reactions using NADP as a coenzyme is further inserted;
[16] A transformant harboring the polynucleotide of [12] or the vector of [14] in an expressible manner;
[17] A method for producing the polypeptide of [13], comprising the step of culturing the transformant of [16];
[18] A method for selectively reducing the carbon-carbon double bonds of α,β-unsaturated ketones comprising the step of reacting the α,β-unsaturated ketones with enzyme active materials selected from the group of: (1) enone reductase of [1]; (2) the polypeptide of [7]; (3) the polypeptide of [13]; (4) a microorganism producing the enzyme or polypeptide; and (5) processed products of the microorganism; and
[19] The method of [18], wherein the microorganism producing the enzyme or polypeptide is the transformant of [10] and/or [16].

DETAILED DESCRIPTION

Figure 1:
FIG. 1 is a photograph showing the electrophoretic pattern of SDS-PAGE. Lane 1 represents the molecular weight marker; lane 2 the enzyme obtained in Example 1.

The present invention provides enzymes having the following physicochemical properties:

(A) Action:
The enzyme reduces the carbon-carbon double bonds of α,β-unsaturated ketones using NADPH as an electron donor to produce a corresponding saturated hydrocarbon.
(B) Substrate specificity:
  (1) the enzyme reduces the carbon-carbon double bonds of α,β-unsaturated ketones but does not substantially have the activity to reduce ketones;
  (2) the enzyme exhibits a significantly higher activity with NADPH than with NADH as the electron donor;
  (3) the enzyme does not substantially act on substrates wherein both substituents at the β carbon relative to the ketone are not hydrogen; and
  (4) the enzyme does not substantially act on substrates wherein the carbon-carbon double bonds are present in the cyclic structure.
(C) Optimal pH:
  pH 6.5–7.0.

Preferably, the enone reductase of the present invention further has the following physicochemical properties:

(D) Optimal temperature:
  37–45° C.;
(E) Molecular weight:

The molecular weight of the reductase determined by sodium dodecyl sulfate-polyacrylamide gel electrophoresis (hereinafter abbreviated as SDS-PAGE) and by gel filtration is about 43,000 Da and about 42,000 Da, respectively.

"The enzyme exhibits a significantly higher activity with NADPH than with NADH" means that the reactivity is at least twice or higher, preferably 3 times or higher, more preferably 5 times or higher. The difference in the relative reactivities to NADPH and NADH can be compared using methods such as those shown in the Examples. Specifically, ketones are generated in the presence of either of these electron donors using the same type of α,β-unsaturated ketone as the substrate. The comparison of reactivity can be conducted by comparing the amounts of consumed NADPH and NADH, respectively.

Further, as used herein, "enone reductase substantially does not have the activity to reduce ketones" or "enone reductase substantially does not act on the substrate" specifically means that the activity is 1% or less of the activity of the reductase to reduce an olefin of a methyl vinyl ketone.

The enzyme of the present invention can be purified from microorganisms producing the enzyme by a standard protein purification method. For example, the enzyme can be purified by lysing the fungal cells, carrying out protamine-sulfate precipitation and centrifugation, salting out the centrifugal supernatant with ammonium sulfate, and then isolating by the combined use of anion exchange chromatography, hydrophobic chromatography, affinity chromatography, gel filtration, etc.

According to the present invention, the enone-reducing activity can be verified as follows. As used herein, "enone" refers to α,β-unsaturated ketones. An exemplary assay for measuring the enone-reducing activity is as follows:

A reaction mixture containing 50 mM potassium phosphate buffer (pH 6.5), 0.2 mM NADPH, 20 mM methyl vinyl ketone, and the enzyme is reacted at 30° C., and the decrease in absorbance at 340 nm, which is associated with the decrease of the amount of NADPH, is measured. 1 U is defined as the amount of enzyme catalyzing a decrease of 1 μmol NADPH in one minute. Quantitative analysis of the polypeptide is conducted by pigment binding methods using the protein assay kit (Bio-Rad Laboratories Inc.).

Enone reductases having physicochemical properties such as those described above can be purified, for example, from cultures of yeast belonging to the genus Kluyveromyces. Kluyveromyces lactis, among yeasts belonging to the genus Kluyveromyces, is particularly excellent in the production of enone reductase of the present invention. Kluyveromyces lactis, for example, IFO 0433, IFO 1012, IFO 1267, IFO 1673, and IFO 1903, can be used to obtain the enone reductase of the present invention, which are available from the Institute for Fermentation, Osaka (IFO).

The above-mentioned microorganisms can be cultured in a medium, such as YM medium, that is generally used for the cultivation of fungi. After well grown, the fungal cells are harvested and lysed in a buffer containing reducing agents, such as 2-mercaptoethanol, and protease inhibitors, such as phenylmethane sulfonylfluoride, to give a cell-free extract. The enzyme can be purified from the cell-free extract by appropriate combinations of fractionation, based on the protein solubility (precipitation with organic solvents, salting out with ammonium sulfate, etc.); and by chromatographies such as cation-exchange, anion-exchange, gel filtration, hydrophobic, and affinity chromatography using chelate, dye, antibody, and so on. The enzyme can be purified as an electrophoretically homogeneous polypeptide, for example, by hydrophobic chromatography using phenyl-Sepharose, anion-exchange chromatography using MonoQ, hydrophobic chromatography using phenyl-Superose, and such.

The enone reductases of the present invention, that can be purified from Kluyveromyces lactis, should have the physicochemical properties described above as (A)–(C) and (D)–(E). The enone reductase of the present invention, that can be purified from Kluyveromyces lactis, is undoubtedly a novel enzyme which is different from α,β-unsaturated carbonyl-compound reductases known in the art.

For example, Clostridium tyrobutyricum-derived 2-enoate reductase (E.C.1.3.1.31) is known as a reductase of α,β-unsaturated carbonyl-compounds. This enzyme reduces (E)-2-methyl-2-butenoic acid in the presence of NADH and produces (R)-2-methylbutyric acid (J. Biotechnol. 6:13–29, 1987). Further, the enzyme acts on substrates, wherein the carbonyl group is contained as carboxylic acid, aldehyde, and keto acid; no activity of acting on ketones has been reported. Furthermore, the molecular weight of this enzyme is 800,000 to 940,000 Da as determined by gel filtration, and thus, is clearly different from the enzyme of the present invention, having a molecular weight is 43,000 Da determined by SDS-PAGE and 42,000 Da by gel filtration.

It has also been reported that a Clostridium kluyveri-derived acryloyl-CoA reductase has an ethyl vinyl ketone reductase activity (Biol. Chem. Hoppe-Seyler 366:953–961, 1985). This enzyme uses a reduced type of methyl viologen as the coenzyme and its molecular weight has been determined to be 28,400 Da by gel filtration and 14,200 Da by SDS-PAGE. Therefore, this enzyme is quite different from the enzyme of the present invention.

In addition, a number of enone reductases purified from baker's yeast are reported. Kawai et al. at Kyoto University have purified an enone reductase (YER-2) from baker's yeast, and reported the enzymological characteristics thereof (The 4$^{th}$ Biocatalyst symposium, Abstract p58 (2001)). The optimal pH of YER-2 for the reaction is pH 7.5, and this indicates that this enzyme is quite different from the enzyme of the present invention (which has an optimal pH of pH 6.5–7.0). Wanner et al. reported the purification and characterization of two types of enone reductases (EI and EII) derived from the same baker's yeast (Eur. J. Biochem. 255:271–278, 1998). EII uses NADH as the coenzyme; and EI is a heterodimer having a molecular weight of 75,000, consisting of two subunits, 34,000 Da and 37,000 Da, as determined by SDS-PAGE. For similar reasons to those above, these enzymes are different from the enzyme of the present invention.

Many enone reductases (verbenone reductase (also referred to as p90), carvone reductase (also referred to as enone reductase-I, enone reductase-II, p44, p74) have been purified from cells of a plant species, tobacco (*Nicotiana tabacum*), and their characteristics have been reported. The verbenone reductase (p90) and p44 have activities to reduce cyclic α,β-unsaturated ketones (J. Chem. Soc., Chem. Commun. 1426–1427, 1993; Chem. Lett. 850–851, 2000), and thus, are different from the enzyme of the present invention. The carvone reductase uses NADH as the coenzyme (Phytochemistry 31:2599–2603, 1992); enone reductase-II can act on compounds, wherein no hydrogen atom exists at the β carbon of the α,β-unsaturated ketone ((R)-pulegone), as the substrate (Phytochemistry 31:2599–2603, 1992); and p74 has a molecular weight of 74,000 Da. Thus, all of these enzymes are quite different from the enzyme of the present invention.

In addition, enone reductases have been also purified from *Euglena gracilis* and *Astasia longa*, which are a kind of plant species (Phytochemistry 49:49–53, 1998). Both of these enzymes use NADH as the coenzyme, and thus are different from the enzyme of the present invention.

Further, with respect to animal species, an enone reductase has been purified from the liver of rat (Arch. Biochem. Biophys. 282:183–187, 1990). This enzyme is a monomeric enzyme with a molecular weight of 39,500. However, the reactivity to cyclic substrates, the reactivity to substrates disubstituted at the β position, the optimal pH, and such properties have not yet been reported.

The present invention relates to isolated polynucleotides encoding an enone reductase and homologues thereof.

As used herein, an "isolated polynucleotide" is a polynucleotide the structure of which is not identical to that of any naturally occurring polynucleotide or to that of any fragment of a naturally occurring genomic polynucleotide spanning more than three separate genes. The term therefore includes, for example, (a) a DNA which has the sequence of part of a naturally occurring genomic DNA molecule in the genome of the organism in which it naturally occurs; (b) a polynucleotide incorporated into a vector or into the genomic DNA of a prokaryote or eukaryote in a manner such that the resulting molecule is not identical to any naturally occurring vector or genomic DNA; (c) a separate molecule such as a cDNA, a genomic fragment, a fragment produced by polymerase chain reaction (PCR), or a restriction fragment; and (d) a recombinant nucleotide sequence that is part of a hybrid gene, i.e., a gene encoding a fusion polypeptide. Specifically excluded from this definition are polynucleotides of DNA molecules present in mixtures of different (i) DNA molecules, (ii) transfected cells, or (iii) cell clones; e.g., as these occur in a DNA library such as a cDNA or genomic DNA library.

Accordingly, in one aspect, the invention provides an isolated polynucleotide that encodes a polypeptide described herein or a fragment thereof. Preferably, the isolated polynucleotide includes a nucleotide sequence that is at least 60% identical to the nucleotide sequence shown in SEQ ID NO:1. More preferably, the isolated nucleic acid molecule is at least 65%, 70%, 75%, 80%, 85%, 90%, 91%, 92%, 93%, 94%, 95%, 96%, 97%, 98%, 99%, or more, identical to the nucleotide sequence shown in SEQ ID NO:1. In the case of an isolated polynucleotide which is longer than or equivalent in length to the reference sequence, e.g., SEQ ID NO:1, the comparison is made with the full length of the reference sequence. Where the isolated polynucleotide is shorter than the reference sequence, e.g., shorter than SEQ ID NO:1, the comparison is made to segment of the reference sequence of the same length (excluding any loop required by the homology calculation).

Herein, the polynucleotides may be composed of naturally occurring polynucleotides, such as DNA and RNA, or they may contain artificially synthesized nucleotide derivatives. There is no restriction on length of the polynucleotide of the present invention, but it preferably comprises at least 15 nucleotides.

A polynucleotide encoding an enone reductase of the present invention comprises, for example, the nucleotide sequence of SEQ ID NO:1. The nucleotide sequence of SEQ ID NO:1 encodes a polypeptide comprising the amino acid sequence of SEQ ID NO:2. This polypeptide, comprising the amino acid sequence of SEQ ID NO:2, is a preferred embodiment of the enone reductase of the present invention. Furthermore, the polynucleotide of the present invention includes those nucleotide sequences which encode the amino acid sequence of SEQ ID NO:2. There are 1 to 6 kinds of codons corresponding to an amino acid, and thus, a polynucleotide encoding the polypeptide consisting of the amino acid sequence of SEQ ID NO:2 is not restricted to the polynucleotide of SEQ ID NO:1, and there are multiple types of polynucleotides that are equivalent to the polynucleotide of SEQ ID NO:1.

The polynucleotides of the present invention include polynucleotides that encode the amino acid sequence of SEQ ID NO:2 in which one or more amino acids are deleted, substituted, inserted and/or added yet which encode a protein having the enzyme activity of an enone reductase. For example, those skilled in the art can introduce substitution, deletion, insertion, and/or addition mutations into the polynucleotide of SEQ ID NO:1 by site-directed mutagenesis (Nucleic Acid Res. 10:6487, 1982; Methods in Enzymol. 100:448, 1983; Molecular Cloning 2$^{nd}$ Ed., Cold Spring Harbor Laboratory Press, 1989; PCR A Practical Approach, IRL Press pp. 200, 1991), and such.

Further, the polynucleotides of the present invention include polynucleotides that hybridize under stringent conditions to the polynucleotide consisting of the nucleotide sequence of SEQ ID NO:1, yet which encode a polypeptide having the enzyme activity of an enone reductase. The phrase "polynucleotides hybridizing under stringent conditions" refers to polynucleotides hybridizing using, for example, ECL direct nucleic acid labeling and detection system (Amersham Pharmacia Biotech) under conditions described in the manual (wash: 42° C., primary wash buffer containing 0.5×SSC) and using polynucleotide(s) selected from one or more sequences containing at least consecutive 20, preferably at least consecutive 30, for example, consecutive 40, 60 or 100 residues arbitrarily selected from the sequence of SEQ ID NO:1 as a probe polynucleotide. Also included in the invention is a polynucleotide that hybridizes under high stringency conditions to the nucleotide sequence of SEQ ID NO:1 or a segment thereof as described herein. "High stringency conditions" refers to hybridization in 6×SSC at about 45° C., followed by one or more washes in 0.2×SSC, 0.1% SDS at 65° C.

Polynucleotides hybridizing under stringent conditions to a polynucleotide consisting of the nucleotide sequence of SEQ ID NO:1 include polynucleotides comprising a nucleotide sequence homologous to that of SEQ ID NO:1. It is highly probable that such polynucleotides encode polypeptides functionally equivalent to the polypeptide consisting of the amino acid sequence of SEQ ID NO:2. Thus, based on the description herein, those skilled in the art can select polynucleotides encoding polypeptides having the enone reductase activity from such polynucleotides.

Further, the polynucleotides of the present invention include polynucleotides that have a percent identity of at least 60%, more preferably at least 70% or 80%, and further more preferably more than 90% to the polynucleotide encoding a polypeptide having the amino acid sequence of SEQ ID NO:2. As used herein, "percent identity" of two amino acid sequences or of two nucleic acids is determined using the algorithm of Karlin and Altschul (Proc. Natl. Acad. Sci. USA 87:2264–2268, 1990) modified as in Karlin and Altschul (Proc. Natl. Acad. Sci. USA 90:5873–5877, 1993). Such an algorithm is incorporated into the NBLAST and XBLAST programs of Altschul et al. (J. Mol. Biol. 215:403–410, 1990). BLAST nucleotide searches are performed with the NBLAST program, score=100, wordlength=12. Homology search of protein can readily be performed, for example, in DNA Databank of JAPAN (DDBJ), by using the FASTA program, BLAST program, etc. BLAST protein searches are performed with the XBLAST program, score=50, wordlength=3. Where gaps exist between two sequences, Gapped BLAST is utilized as described in Altsuchl et al. (Nucleic Acids Res. 25:3389–3402, 1997). When utilizing BLAST and Gapped BLAST programs, the default parameters of the respective programs (e.g., XBLAST and NBLAST) are used. Homology search of proteins can be achieved, for example, on the Internet by using programs such as BLAST, FASTA, and such, for example, in databases related to amino acid sequence of polypeptides, such as SWISS-PROT, PIR, and such; databases related to polynucleotide sequences, such as DDBJ, EMBL, GenBank, and such; databases related to deduced amino acid sequences based on polynucleotide sequences; and so on. As a result of homology search in SWISS-PROT for the amino acid sequence of SEQ ID NO:2 by using BLAST program, *Cochliobolus carbonum* tox D protein exhibited the highest percent identity (36% (Identity) and 54% positives)) among known polypeptides. Herein, a percent identity over 60% indicates, for example, the value of percent identity in Positive using BLAST program.

According to the BLAST search, potential open reading frames (ORFs), whose functions are unknown, having homology to the enone reductase of the present invention have been revealed. More specifically, three types of potential ORFs were given by genomic analysis of *Saccharomyces cerevisiae*, named YNN4, YL60, and YCZ2, respectively. Percent identity scores of these deduced amino acid sequences to the enone reductase of the present invention were 54%, 51%, and 53% (identity); and 69%, 68%, and 69% (positive), respectively. In order to clarify whether these deduced polypeptides have the enone reductase activity of the present invention, primers were synthesized based on the polynucleotide sequences deposited in the DDBJ, and the regions of potential ORFs were cloned by PCR from the genomic DNA of *Saccharomyces cerevisiae*. Each ORF was inserted in an expression vector, and *E. coli* was transformed with the vector. The resulting transformant was cultured, and each polypeptide was expressed. As a result, it was confirmed that all YNN4, YL60, and YCZ2 have the enone-reducing activity. These results confirm the validity of the presumption that a polypeptide exhibiting 60% or higher percent identity to the amino acid sequence of SEQ ID NO:2 has the enone reducing activity of the present invention. The nucleotide sequences and amino acid sequences of YNN4, YL60, and YCZ2 are shown with the following SEQ ID NOs. There is no previous report that these ORFs encode polypeptides having an enone reductase activity.

|  | Nucleotide sequence | Amino acid sequence |
|---|---|---|
| YNN4 | SEQ ID NO:3 | SEQ ID NO:4 |
| YL60 | SEQ ID NO:5 | SEQ ID NO:6 |
| YCZ2 | SEQ ID NO:7 | SEQ ID NO:8 |

The polynucleotides of the present invention include polynucleotides comprising the nucleotide sequences of SEQ ID NO:3, SEQ ID NO:5, and SEQ ID NO:7. In addition, the present invention includes all polynucleotides comprising the nucleotide sequences encoding the amino acid sequences encoded by these polynucleotides, as well as the amino acid sequences of SEQ ID NO:4, SEQ ID NO:6 and SEQ ID NO:8. Further, the present invention includes polynucleotides encoding polypeptides functionally equivalent to the polypeptides consisting of the amino acid sequences of SEQ ID NO:4, SEQ ID NO:6, and SEQ ID NO:8.

More specifically, the polynucleotides of the present invention include polynucleotides encoding a polypeptide including any one of the amino acid sequences according to SEQ ID NO:4, SEQ ID NO:6, and SEQ ID NO:8, wherein one or more amino acids have been deleted, substituted, inserted and/or added, further wherein said encoded polypeptide has the enone reductase activity. Such polynucleotides can be obtained according to the method as described above.

Further, the polynucleotides of the present invention include polynucleotides hybridizing under stringent conditions to any one of the polynucleotides consisting of the nucleotide sequence of SEQ ID NO:3, SEQ ID NO:5, and SEQ ID NO:7, yet which encode a polypeptide having the enzyme activity of enone reductase. The "polynucleotides hybridizing under stringent conditions" refers to polynucleotides using, for example, the ECL direct nucleic acid labeling and detection system (Amersham Pharmacia Biotech) under conditions described in the manual (wash: 42° C., primary wash buffer containing 0.5×SSC), and using polynucleotides selected from one or more sequences containing at least consecutive 20, preferably at least consecutive 30, for example, consecutive 40, 60 or 100 residues that are arbitrarily selected from the sequences of SEQ ID NO:3, SEQ ID NO:5, and SEQ ID NO:7 as probe polynucleotides. Also included in the invention is a polynucleotide that hybridizes under high stringency conditions to the nucleotide sequence of SEQ ID NO:3, SEQ ID NO:5, or SEQ ID NO:7, or a segment thereof as described herein. "High stringency conditions" refers to hybridization in 6×SSC at about 45° C., followed by one or more washes in 0.2×SSC, 0.1% SDS at 65° C.

The polynucleotides hybridizing under stringent conditions to a polynucleotide consisting of the nucleotide sequence of SEQ ID NO:3, SEQ ID NO:5, or SEQ ID NO:7 include polynucleotides which are homologous to these polynucleotides. It is highly probable that such polynucleotides encode polypeptides functionally equivalent to the polypeptide consisting of the amino acid sequence of SEQ ID NO:4, SEQ ID NO:6, or SEQ ID NO:8.

Further, the polynucleotides of the present invention include polynucleotides encoding polypeptides having at least 60%, preferably at least 70% or 80%, more preferably 90% or higher percent identity to the amino acid sequence of SEQ ID NO:4, SEQ ID NO:6, or SEQ ID NO:8. Protein homology search can be carried out by such methods as described above.

The polynucleotides of the present invention are useful for the production of the enone reductases of the present invention by genetic engineering. With the polynucleotide of the present invention, it is also possible to create genetically engineered microorganisms having the enone reductase activity that are useful in the production of an α,β-saturated ketone from an α,β-unsaturated ketone.

The present invention includes a substantially pure polypeptide comprising the amino acid sequence of SEQ ID NO:2, wherein the polypeptide has the enone reductase activity, as well as homologues thereof. The polypeptide comprising the amino acid sequence of SEQ ID NO:2 constitutes a preferred embodiment of enone reductases of the present invention.

The term "substantially pure" as used herein in reference to a given polypeptide means that the polypeptide is substantially free from other biological macromolecules. The substantially pure polypeptide is at least 75% (e.g., at least 80, 85, 95, or 99%) pure by dry weight. Purity can be measured by any appropriate standard method, for example by column chromatography, polyacrylamide gel electrophoresis, or HPLC analysis.

Homologues of the enone reductase of the present invention include enzymes having the amino acid sequence of SEQ ID NO:2, in which one or more amino acids are deleted, substituted, inserted and/or added. Those skilled in the art can readily obtain polynucleotides encoding such homologues of the enone reductase by properly introducing substitution, deletion, insertion, and/or addition mutations into the polynucleotide of SEQ ID NO:1 by site-directed mutagenesis (Nucleic Acid Res. 10:6487, 1982; Methods in Enzymol. 100:448, 1983; Molecular Cloning 2$^{nd}$ Ed., Cold Spring Harbor Laboratory Press, 1989; PCR A Practical Approach, IRL Press pp. 200, 1991), and so on.

The number of amino acids that are mutated is not particularly restricted, as long as the enone reductase activity is maintained. Normally, it is within 50 amino acids, preferably within 30 amino acids, more preferably within 10 amino acids, and even more preferably within 3 amino acids. The site of mutation may be any site, as long as the (R)-2,3-butanediol dehydrogenase activity is maintained.

An amino acid substitution is preferably mutated into different amino acid(s) in which the properties of the amino acid side-chain are conserved. A "conservative amino acid substitution" is a replacement of one amino acid residue belonging to one of the following groups having a chemically similar side chain with another amino acid in the same group. Groups of amino acid residues having similar side chains have been defined in the art. These groups include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine).

Further, the homologues of the enone reductase of the present invention includes polypeptides having an amino acid sequence exhibiting at least 60%, preferably at least 70% or 80%, more preferably 90% or higher percent identity to the amino acid sequence of SEQ ID NO:2. Homology search of protein can be achieved, for example, on the Internet using programs such as BLAST, FASTA, and such, for example, in databases related to amino acid sequence of polypeptides, such as SWISS-PROT, PIR, and such; databases related to polynucleotide sequences, such as DDBJ, EMBL, GenBank, and such; databases related to deduced amino acid sequences based on polynucleotide sequences; and so on. As a result of homology search in DDBJ for the amino acid sequence of SEQ ID NO:2 by using BLAST program, Cochliobolus carbonum tox D protein exhibited the highest percent identity (36% (Identity) and 54% positives)) among known polypeptides. Herein, 60% or higher percent identity indicates, for example, the value of percent identity in Positive using BLAST program.

Potential open reading frames (ORFs), whose functions are unknown, having homology to the enone reductase of the present invention were revealed by the BLAST search. Specifically, three types of potential ORFs given by genomic analysis of Saccharomyces cerevisiae, which have been named YNN4, YL60, and YCZ2 were obtained. Percent identity scores of these deduced amino acid sequences to the enone reductase of the present invention were 54%, 51%, and 53% (identity); and 69%, 68%, and 69% (positive), respectively. In order to clarify whether these candidate polypeptides have the enone reductase activity of the present invention, primers were synthesized based on the polynucleotide sequences deposited in the DDBJ, and the regions of potential ORFs were cloned by PCR from the genomic DNA of Saccharomyces cerevisiae. Each ORF was inserted in an expression vector, and E. coli was transformed with the vector. The resulting transformant was cultured, and each polypeptide was expressed. As a result, all of the polypeptides of YNN4, YL60, and YCZ2 were confirmed to have the enone-reducing activity. These results confirm the validity of presumption that a polypeptide exhibiting 60% or higher percent identity to the amino acid sequence of SEQ ID NO:2 has the enone-reducing activity of the present invention.

Namely, a polypeptide comprising any one of the amino acid sequences of SEQ ID NO:4, SEQ ID NO:6, and SEQ ID NO:8 constitutes a preferred embodiment of an enone reductase of the present invention.

Polynucleotides encoding an enone reductase of the present invention can be isolated, for example, by the following method.

The polynucleotides of the present invention can be isolated from other organisms by PCR cloning or hybridization based on the nucleotide sequence of SEQ ID NO:1. The nucleotide sequence of SEQ ID NO:1 is a sequence of a gene isolated from Kluyveromyces lactis. Polynucleotides encoding polypeptides having the enone reductase activity can be obtained from microorganisms, such as yeasts belonging to the genus Kluyveromyces and the genus Saccharomyces, by first designing PCR primers based on the nucleotide sequence of SEQ ID NO:1. For example, as described above, a polynucleotide having the nucleotide sequence of SEQ ID NO:3, SEQ ID NO:5, and SEQ ID NO:7 that can be isolated from Saccharomyces cerevisiae by PCR encodes a polypeptide having the enone reductase activity of the present invention. Alternatively, polynucleotides encoding polypeptides having a similar enzyme activity can be derived from other species using the polynucleotides, whose nucleotide sequences have already been revealed, as a probe.

Alternatively, the polynucleotides of the present invention can be obtained by utilizing the structural features of the isolated enone reductase having the physicochemical properties described above in (A) to (C). Following the purification of the enzyme of the present invention, the N-terminal amino acid sequence is determined. Furthermore, multiple amino acid sequences can be determined by analyzing with a protein sequencer the polypeptide fragments purified by reverse-phase liquid chromatography and such, following the digestion of the purified polypeptide with enzymes, such as lysylendopeptidase and V8 protease.

Once the partial amino acid sequences are clarified, then the encoding nucleotide sequence can be estimated. PCR primers are designed based on the putative nucleotide sequence or the nucleotide sequence of SEQ ID NO:1, and then, a part of a polynucleotide of the present invention can be obtained by conducting PCR using genomic DNAs or cDNA libraries of enzyme-producing strains as the template.

Moreover, a polynucleotide of the present invention can be obtained using an obtained polynucleotide fragment as the probe, and by conducting colony hybridization, plaque hybridization, and so on, using libraries and cDNA libraries constructed by inserting the restriction enzyme digestion product of the genomic DNA of an enzyme-producing strain into a phage, plasmid, and such, and transforming E. coli therewith.

It is also possible to obtain a polynucleotide of the present invention by analyzing the nucleotide sequence of an obtained polynucleotide fragment by PCR, designing PCR primers to elongate the known polynucleotide, and after digesting the genomic DNA of the enzyme-producing strain with an appropriate restriction enzyme, reverse PCR is performed using the DNA as the template by a self cyclization reaction (Genetics 120, 621–623 (1988)), the RACE method (Rapid Amplification of cDNA End, "PCR experimental manual" p25–33 HBJ press), and such.

The polynucleotide of the present invention include not only genomic DNA or cDNA cloned by the above-mentioned methods but also synthesized polynucleotides.

An enone reductase-expressing vector is provided by inserting the isolated polynucleotide encoding an enone reductase of the present invention into a known expression vector. Further, by culturing cells transformed with the expression vector, the enone reductase of the present invention can be obtained from the transformed cells.

The recombinant vectors of the present invention also include recombinant vectors wherein, in addition to a polynucleotide encoding the enone reductase of the present invention, a polynucleotide encoding a dehydrogenase catalyzing an oxidation reaction using NADP as a coenzyme is inserted. Such dehydrogenases include glucose dehydrogenase, glutamate dehydrogenase, formate dehydrogenase, malate dehydrogenase, glucose-6-phosphate dehydrogenase, phosphogluconate dehydrogenase, alcohol dehydrogenase, glycerol dehydrogenase, and so on. These enzymes can be used to regenerate NADPH, the coenzyme of the enone reductases of the present invention, from $NADP^+$.

Herein, there is no restriction on the microorganism to be transformed for expressing the enone reductase, whose coenzyme is NADPH, so long as the microorganism is transformed with a recombinant vector containing a polynucleotide encoding a polypeptide having the enone reductase activity whose coenzyme is NADPH, and can express the enone reductase activity which coenzyme is NADPH. Useful microorganisms are those for which a host-vector system is available and include, for example, organisms such as:

bacteria such as the genus Escherichia, the genus Bacillus, the genus Pseudomonas, the genus Serratia, the genus Brevibacterium, the genus Corynebacterium, the genus Streptococcus, and the genus Lactobacillus;

actinomycetes such as the genus Rhodococcus, and the genus Streptomyces;

yeasts such as the genus Saccharomyces, the genus Kluyveromyces, the genus Schizosaccharomyces, the genus Zygosaccharomyces, the genus Yarrowia, the genus Trichosporon, the genus Rhodosporidium, the genus Pichia, and the genus Candida; and fungi such as the genus Neurospora, the genus Aspergillus, the genus Cephalosporium, and the genus Trichoderma.

The preparation of a transformant and construction of a recombinant vector suitable for the host can be carried out by employing conventional techniques used in the fields of molecular biology, bioengineering, and genetic engineering (for example, see Sambrook et al., "Molecular Cloning", Cold Spring Harbor Laboratories). In order to express a gene encoding an enone reductase of the present invention, whose coenzyme is NADPH, in a microorganism, it is necessary to first introduce the polynucleotide into a plasmid vector or phage vector that is stable in the microorganism and allow the genetic information to transcribe and translate. Therefore, a promoter, a unit for regulating the transcription and translation, is placed upstream of the 5'-end of the polynucleotide strand of the present invention, and a terminator is preferably placed downstream of the 3'-end of the polynucleotide strand. The promoter and the terminator should be functional in the microorganism to be utilized as the host. Available vectors, promoters, and terminators for the above-mentioned various microorganisms are described in detail in "Fundamental Course in Microbiology (8): Genetic Engineering", Kyoritsu Shuppan, and those specifically for yeasts in "Adv. Biochem. Eng. 43, 75–102 (1990)", "Yeast 8, 423–488 (1992)", and such.

For example, for the genus Escherichia, in particular for *Escherichia coli*, available plasmids include the pBR series and pUC series plasmids; available promoters include promoters derived from lac (derived from β-galactosidase gene), trp (derived from the tryptophan operon), tac, trc (which are chimeras of lac and trp), $P_L$ and $P_R$ of λ phage, etc. Terminators derived from trpA, phages, rrnB ribosomal RNA, and so on are available. The vector pSE420D (described in the Unexamined Published Japanese Patent Application No. (JP-A) 2000-189170), which is a vector constructed by partially modifying the multicloning site of the commercially available pSE420 (Invitrogen), can be preferably used.

The pUB110 series, pC194 series plasmids, and so on can be used for the genus Bacillus. The vectors can be integrated into the host chromosome. Available promoters and terminators are derived from apr (alkaline protease), npr (neutral protease), amy (α-amylase), etc.

For the genus Pseudomonas, host-vector systems for *Pseudomonas putida* and *Pseudomonas cepacia* have been developed. A broad-host-range vector, pKT240 (containing genes required for autonomous replication derived from RSF1010, and such) based on TOL plasmid, which is involved in the decomposition of toluene compounds, is available; the promoter and terminator derived from the lipase gene (JP-A Hei 5-284973) are available.

Plasmid vectors, such as pAJ43 (Gene 39:281, 1985), are available for the genus Brevibacterium, in particular for *Brevibacterium lactofermentum*. Promoters and terminators used for *Escherichia coli* can be also utilized for Brevibacterium without any modification.

Plasmid vectors, such as pCS11 (JP-A Sho 57-183799) and pCB101 (Mol. Gen. Genet. 196:175, 1984), are available for the genus Corynebacterium, in particular, for *Corynebacterium glutamicum*.

Plasmid vectors, such as pHV1301 (FEMS Microbiol. Lett. 26:239, 1985) and pGK1 (Appl. Environ. Microbiol. 50:94, 1985), can be used for the genus Streptococcus.

Plasmid vectors, such as pAMβ1 (J. Bacteriol. 137:614, 1979), which was developed for the genus Streptococcus, can be utilized for the genus Lactobacillus; and promoters used for *Escherichia coli* can be utilized.

Plasmid vectors isolated from *Rhodococcus rhodochrous* (J. Gen. Microbiol. 138:1003, 1992) are available for the genus Rhodococcus.

Plasmids for the genus Streptomyces can be constructed according to the methods described in "Genetic Manipulation of Streptomyces: A Laboratory Manual"(Cold Spring Harbor Laboratories, 1985) by Hopwood et al. In particular, pIJ486 (Mol. Gen. Genet. 203:468–478, 1986), pKC1064 (Gene 103:97–99, 1991), and pUWL-KS (Gene 165:149–150, 1995) can be used for *Streptomyces lividans*. The same plasmids may be also utilized for *Streptomyces virginiae* (Actinomycetol. 11:46–53, 1997).

The YRp series, YEp series, YCp series, and YIp series plasmids are available for the genus Saccharomyces, in particular, for *Saccharomyces cerevisiae*. Integration vectors (refer EP 537456, etc.) that utilize the homologous recombination with the ribosomal DNA, many copies of which exist on the chromosome, allow introduction of genes of interest in multicopy and those genes incorporated are stably maintained in the microorganism; thus, these types of vectors are highly useful. Promoters and terminators derived from genes encoding ADH (alcohol dehydrogenase), GAPDH (glyceraldehyde-3-phosphate dehydrogenase), PHO (acid phosphatase), GAL (β-galactosidase), PGK (phosphoglycerate kinase), ENO (enolase), and so on can be utilized.

For the genus Kluyveromyces, in particular, for *Kluyveromyces lactis*, plasmids such as 2μm series plasmids derived from *Saccharomyces cerevisiae*; the pKD1 series plasmids (J. Bacteriol. 145:382–390, 1981); plasmids derived from pGK11 involved in the killer activity, KARS (Kluyveromyces autonomous replication sequence) series plasmids; and vector plasmids (refer EP 537456, etc.), which can be integrated into the chromosome through the homologous recombination with the ribosomal DNA and such, are available. Promoters and terminators derived from ADH, PGK, and the like are available.

Plasmid vectors comprising the ARS (autonomous replication sequence) derived from *Schizosaccharomyces pombe* and the auxotrophy-complementing selectable markers derived from *Saccharomyces cerevisiae* (Mol. Cell. Biol. 6:80, 1986) are available for the genus Schizosaccharomyces. Promoters such as ADH promoter derived from *Schizosaccharomyces pombe* may be used (EMBO J. 6:729, 1987). In particular, pAUR224 is commercially available from TaKaRa Shuzo Co., Ltd., and thus, can be used readily.

Plasmid vectors originating from pSB3 (Nucleic Acids Res. 13:4267, 1985); derived from *Zygosaccharomyces rouxii*), and such are available for the genus Zygosaccharomyces. Promoters such as PHO5 promoter derived from *Saccharomyces cerevisiae* and GAP-Zr (Glyceraldehyde-3-phosphate dehydrogenase) promoter (Agri. Biol. Chem. 54:2521, 1990) derived from *Zygosaccharomyces rouxii* can be used.

Host vector systems utilizing Pichia-derived genes involved in autonomous replication (PARS1 and PARS2) are developed for the genus Pichia, especially for *Pichia pastoris* and such (Mol. Cell. Biol. 5:3376, 1985), and thus, strong promoters such as AOX, which can be cultivated to high-density and are inducible with methanol (Nucleic Acids Res. 15:3859, 1987) are available. Additionally, another host-vector system has been developed for *Pichia angusta* (previously called *Hansenula polymorpha*) among the genus Pichia. Vectors including *Pichia angusta*-derived genes (HARS1 and HARS2) involved in autonomous replication are also useful; however, they are relatively unstable. Therefore, multi-copy integration of the gene into the chromosome is effective (Yeast 7:431–443, 1991). Promoters of AOX (alcohol oxidase) and FDH (formic acid dehydrogenase), which are induced by methanol and such, are also available.

For the genus Candida, host-vector systems have been developed for *Candida maltosa, Candida albicans, Candida tropicalis, Candida utilis*, etc. An autonomous replication sequence (ARS) originating from *Candida maltosa* has been cloned (Agri. Biol. Chem. 51:1587, 1987), and a vector using the sequence has been developed for *Candida maltosa*. Further, a chromosome-integration vector with a highly efficient promoter unit has been developed for *Candida utilis* (JP-A Hei. 08-173170).

In relation to the genus Aspergillus, *Aspergillus niger* and *Aspergillus oryzae* have been intensively studied among fungi, and thus, both plasmid vectors and chromosome-integration vectors are available. Furthermore, promoters derived from an extracellular protease gene and amylase gene (Trends in Biotechnology 7:283–287, 1989) are available.

Host-vector systems have been developed for *Trichoderma reesei* of the genus Trichoderma, and promoters such as those derived from an extracellular cellulase gene, and such are available (Biotechnology 7:596–603, 1989).

There are various host-vector systems developed for plants and animals other than microorganisms; in particular, the systems include those of insect, such as silkworm (Nature 315:592–594, 1985), and plants, such as rapeseed, maize, potato, etc. These systems are preferably employed to express a large amount of foreign polypeptides.

Further, transformants expressing an enone reductase of the present invention obtained by the above methods can be used to produce an enzyme of the present invention, as well as to produce α,β-saturated ketone by selective reduction of the carbon-carbon double bond of α,β-unsaturated ketone as described below.

Namely, the present invention relates to methods for selectively reducing the carbon-carbon double bond of α,β-unsaturated ketone, which comprises the step of reacting the α,β-unsaturated ketone with any one of the materials exhibiting the enzymatic activity selected from the group consisting of the above-mentioned enone reductases, microorganisms producing the enzymes or polypeptides, and processed products of the microorganisms. The desired enzyme reaction can be carried out by contacting the reaction solution with an enzyme of the present invention, a culture containing an enzyme, or processed products thereof.

According to the method of the present invention, polypeptides comprising the amino acid sequence of SEQ ID NO:2, homologues thereof, and enone reductases having the above physicochemical properties (A) to (C) can be used as enone reductases. Not only purified enone reductases but also crude enzymes are usable. Further, cells producing the enone reductase can be also used as an enone reductase according to the present invention. All strains belonging to the genus Kluyveromyces, mutant strains, variants, and genetically engineered transformants that have acquired the productivity of enzyme of the present invention, which can produce the NADPH-dependent enone reductase are included as enone reductase producing cells to be used in the present invention. The enone reductase producing cells can be used in the form of the culture, cells separated from the culture medium by filtration, centrifugation or the like, or cells resuspended in buffer, water, or the like after they are separated by centrifugation and washed. The separated cells can be used in a state as they are recovered, as their disrupts, as treated with acetone or toluene, or as lyophilizate. When the enzyme is extracellularly produced, the culture medium of the cells can also be used after it is separated from the cells by the usual methods.

The means by which the enzymes and the reaction solutions are contacted is not limited to these specific examples. The reaction solution comprises substrates and NADPH, a coenzyme required for the enzyme reaction, dissolved in a suitable solvent that gives an environment desirable for enzyme activity. Specific examples of processed products of microorganisms containing an enone reductase of the present invention include: microorganisms, wherein the permeability of the cell membrane has been altered by detergents or organic solvents, such as toluene; cell-free extracts obtained by lysing the microorganism with glass beads or by enzyme treatment; partially purified material of the cell-free extracts; and so on.

There is no limitation on the α,β-unsaturated ketones of the present invention. For example, the α,β-unsaturated ketones include compounds represented by the following formula I;

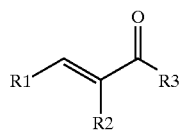

wherein:
R1 is a substituted or unsubstituted alkyl group, a substituted or unsubstituted alkenyl group, a substituted or unsubstituted aralkyl group, or a substituted or unsubstituted alkoxy group;
R2 is hydrogen, or a substituted or unsubstituted short-chain alkyl group; and
R3 is a substituted or unsubstituted short-chain alkyl group.

More specifically, methyl vinyl ketone, ethyl vinyl ketone, 3-penten-2-one, 3-methyl-3-penten-2-one, and such are suitably used.

Further, the enzyme can also be utilized for the synthesis of optically active saturated ketones by allowing the enzymes of the present invention, microorganisms producing the enzyme, or processed products thereof to react on α,β-unsaturated ketones containing α-substitution.

An NADPH regeneration system can be combined with the method for producing ketones according to the above-mentioned present invention. The reduction by enone reductases accompanies generation of $NADP^+$ from NADPH. Regeneration of NADPH from $NADP^+$ can be achieved by using enzymes (systems) regenerating NADPH from $NADP^+$ contained in microorganisms. It is possible to enhance the ability of the enzymes (systems) to reduce $NAPD^+$ by adding glucose or ethanol into the reaction system. Furthermore, NADPH can be regenerated using microorganisms including enzymes which have the ability to generate NADPH from $NAPD^+$, for example, glucose dehydrogenase, glutamate dehydrogenase, formic acid dehydrogenase, malate dehydrogenase, glucose-6-phosphate dehydrogenase, phosphogluconate dehydrogenase, alcohol dehydrogenase, glycerol dehydrogenase, and so on; and processed products thereof; as well as partly purified and purified enzymes. For example, the regeneration of NADPH can be achieved by using the conversion of glucose to δ-gluconolactone catalyzed by the above glucose dehydrogenase.

The components required for the reaction to regenerate NADPH can be added or added after immobilization on a solid phase to the reaction system to produce ketones in accordance with the present invention. Alternatively, they can be contacted via a membrane which permeates NADH.

Furthermore, in some cases where living microorganism transformed with recombinant vectors containing the polynucleotide of the present invention are used in the production of ketones described above, additional reaction systems for the regeneration of NADPH are unnecessary. Specifically, efficient reaction can be achieved without the addition of enzymes for the regeneration of NADPH by using microorganisms that have a higher activity for regenerating NADPH in the reduction reaction with transformants. Furthermore, it is possible to conduct a more efficient reaction to express the NADPH regenerating enzymes and NADPH-dependent enone reductases, and to conduct a more efficient reduction reaction by co-introducing a gene encoding glucose dehydrogenase, formic acid dehydrogenase, alcohol dehydrogenase, amino acid dehydrogenase, organic acid dehydrogenase (e.g., malate dehydrogenase), or the like, which can be utilized in the regeneration of NADPH, together with a polynucleotide encoding the NADPH-dependent enone reductase of the present invention into a host. Several methods are available for introducing these two genes or more into a host, including methods to transform a host with multiple recombinant vectors derived from different origins separately inserted with each gene to avoid incompatibility in *E. coli*; methods wherein both genes are inserted into a single vector; methods wherein either or both genes are introduced into the chromosome; and so on.

*Bacillus subtilis*-derived glucose dehydrogenase can be mentioned as a glucose dehydrogenases that can be used to regenerate NADPH in the present invention. The gene encoding the enzyme has been already isolated. Based on the known nucleotide sequence, the gene can also be obtained from the microorganism by PCR or hybridization screening.

When multiple genes are intended to be inserted into a single vector, they can be expressed by methods wherein the control regions associated with expression, such as promoter and terminator, are ligated with each gene and by methods wherein the genes are expressed as operons containing multiple cistrons, such as lactose operon.

The reduction reaction using an enzyme of the present invention may be performed in water or in a two-solvent system consisting of water and organic solvent that is not miscible with water. For example, ethyl acetate, butyl acetate, toluene, chloroform, n-hexane, isooctane, and such are included as usable organic solvents that is not miscible with water. Alternatively, the reaction can be also carried out in a mixed solvent system consisting of aqueous solvent and organic solvent such as ethanol, acetone, dimethyl sulfoxide, acetonitrile, etc.

The reaction of the present invention can be also conducted by using immobilized enzymes, membrane reactors, and so on. α,β-unsaturated ketones used as substrates in the reaction are often insoluble in water. Therefore, the inhibitory effects of the substrate and product can be reduced by contacting and reacting the aqueous phase containing the enzyme of the present invention, microorganism containing the enzyme of the present invention, or processed products thereof with the organic solvent phase containing the substrate, α,β-unsaturated ketone, through a hydrophobic membrane, such as polypropylene membrane.

The enzyme reaction of the enone reductase of the present invention can be carried out under the following condition:

reaction temperature: 4 to 55° C., preferably 10 to 45° C.;

pH: 4 to 9, preferably 5.5 to 8, more preferably pH6.5 to 7.0; and substrate concentration: 0.01 to 90%, preferably 0.1 to 20%.

The coenzyme $NADP^+$ or NADPH can be added at a concentration of 0.001 mM to 100 mM, preferably 0.01 to 10 mM, to the reaction system, according to needs. The substrate can be added once at the start of reaction, but it is preferably added continuously or stepwise to prevent the substrate concentration in the reaction solution from becoming too high.

Compounds added to the reaction system to regenerate NADPH (e.g., glucose when glucose dehydrogenase is used, formic acid when formate dehydrogenase is used, ethanol or 2-propanol when alcohol dehydrogenase is used, L-glutamic acid when glutamate dehydrogenase is used, and L-malic acid when malate dehydrogenase is used, etc.) can be added at a molar ratio of 0.1–20, preferably 0.5–5 to the substrate, α,β-unsaturated ketone. The enzymes for regenerating NADPH, for example, glucose dehydrogenase, formate dehydrogenase, alcohol dehydrogenase, amino acid dehydrogenase, organic acid dehydrogenase (malate dehydrogenase, etc.), and such, can be added at an enzymatic activity of 0.1–100 folds, preferably 0.5–20 folds as compared to the enzymatic activity of the NADPH-dependent enone reductase of the present invention.

The purification of ketone generated by the reduction of α,β-unsaturated ketone according to the present invention can be performed by properly combining centrifugation of fungal cells and polypeptides, separation with membrane and such, extraction by solvent, distillation, chromatography, and so on.

The enzymes of the present invention to be used in various synthetic reactions and are not restricted to purified enzymes. They also include partially purified enzymes, cells of microorganisms containing the enzyme, processed products thereof, and so on. The processed product of the present invention includes cells of microorganisms, purified enzymes, partially purified enzymes, and such, that are immobilized by various methods. The immobilization can be achieved by a known method such as sulfur-containing polysaccharide (e.g., κ-carrageenan), calcium alginate, agar gel method, and polyacrylamide gel method.

Novel enone reductases that selectively reduce the carbon-carbon double bond of α,β-unsaturated ketone are provided. Ketones useful as a raw material for pharmaceuticals can be enzymatically produced using such enzymes. The enone reductases of the present invention have high selectivity toward the carbon-carbon double bond of α,β-unsaturated ketone. Therefore, the ketone of interest can be prepared at a high yield.

Any patents, patent applications, and publications cited herein are incorporated by reference.

The present invention is illustrated in detail below with reference to Examples, but is not to be construed as being limited thereto.

Herein, "%" for concentration denotes weight per volume percent unless otherwise specified.

EXAMPLE 1

Purification of Enone Reductase

*Kluyveromyces lactis*, IFO 1267 strain, was cultured in 1.2 L of YM culture medium (20 g/L glucose, 3 g/L yeast extract, 3 g/L wheat germ extract, 5 g/L peptone; pH 6.0). The fungal cells were harvested by centrifugation. The resulting wet fungal cells were suspended in a solution consisting of 50 mM potassium phosphate buffer (pH 8.0), 0.02% 2-mercaptoethanol, and 2 mM phenyl methane sulfonylfluoride (PMSF), and then, crushed with a bead-beater (Biospec). Then, fungal-cell debris was removed by centrifugation and the cell-free extract was obtained. Nucleic acid-free supernatant was prepared by adding protamine sulfate to the cell-free extract followed by centrifugation of the mixture. Ammonium sulfate was added to the supernatant to 30% saturation. The supernatant was loaded onto a column of phenyl-Sepharose HP (2.6 cm×10 cm) equilibrated with a standard buffer (10 mM Tris-HCl buffer (pH 8.5), 0.01% 2-mercaptoethanol, 10% glycerol) containing 30% ammonium sulfate; the elution was performed with a concentration gradient of 30 to 0% ammonium sulfate.

The NADPH-dependent methyl vinyl ketone reducing activity was eluted as two peaks by the elution with the concentration gradient. Eluted fractions corresponding to the second peak of the two were collected, and were concentrated by ultrafiltration.

The concentrated enzyme solution was dialyzed against the standard buffer, and then, was loaded onto the MonoQ (0.5 cm×5 cm) equilibrated with the same buffer. After the column was washed with the standard buffer, elution was carried out with a concentration gradient of 0–0.5 M sodium chloride. The eluted active fractions were collected, and were concentrated by ultrafiltration.

Ammonium sulfate was added to the concentrated enzyme solution at 30% saturation. The solution was loaded onto the phenyl-Superose (0.5 cm×5 cm) equilibrated with the standard buffer containing 30% saturated ammonium sulfate. After the column was washed with the same buffer, elution with a gradient of saturated ammonium sulfate of 30–0% was carried out. The eluted active fractions were collected.

The active fractions obtained by using the phenyl-Superose were analyzed by SDS-PAGE; the fraction gave a single band (FIG. 1).

Specific activity of the purified enzyme was about 31.7 U/mg. The purification processes are summarized in Table 1.

TABLE 1

| Step | Protein (mg) | Enzyme activity (U) | Specific activity (U/mg) |
| --- | --- | --- | --- |
| Cell-free extract | 3390 | 1360 | 0.401 |
| Protamine sulfate precipitation | 1480 | 1220 | 0.851 |
| Phenyl-Sepharose | 156 | 222 | 1.42 |
| MonoQ | 2.70 | 117 | 43.4 |
| Phenyl-Superose | 0.162 | 5.14 | 31.7 |

EXAMPLE 2

Molecular Weight Determination of Enone Reductase

The molecular weight of the subunit of the enzyme obtained in Example 1 was determined to be 43,000 by SDS-PAGE. Further, the molecular weight determined by using a gel filtration column, Superdex G200, was approximately 42,000. Therefore, the enone reductase of the present invention was predicted to be a monomer.

EXAMPLE 3

Optimal pH of Enone Reductase

Figure 2:
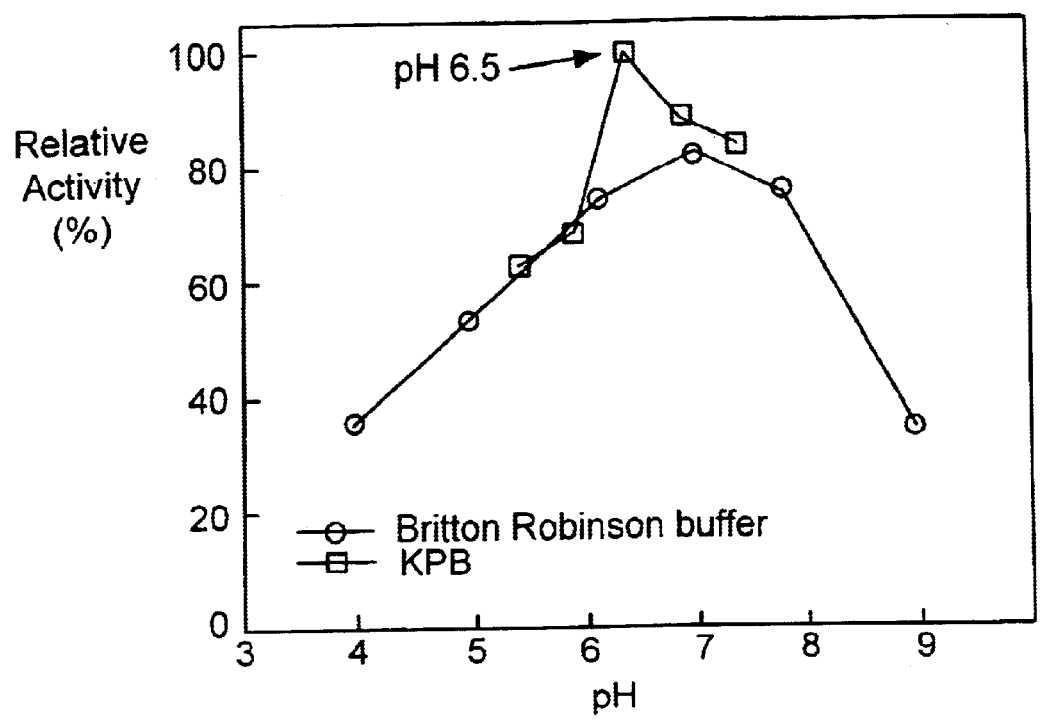
FIG. 2 shows the pH dependency of the methyl vinyl ketone-reducing activity of the enzyme obtained in Example 1.

The methyl vinyl ketone-reducing activity of the enzyme obtained in Example 1 was tested, by altering the pH of the reaction with potassium phosphate buffer and Britton Robinson buffer. The activity is represented by a relative activity, taking the maximal activity as 100, and the results are shown in FIG. 2. The optimal pH for the reaction was determined to be 6.5 to 7.0.

EXAMPLE 4

Optimal Temperature for Enone Reductase

Figure 3:
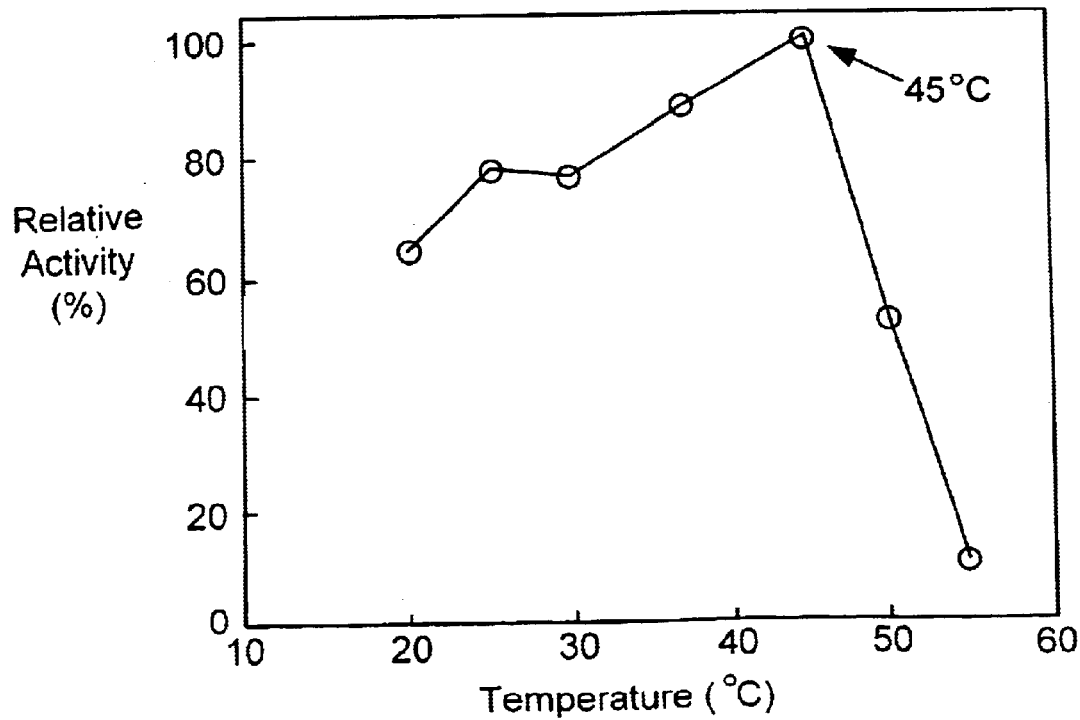
FIG. 3 shows the temperature dependency of the methyl vinyl ketone-reducing activity of the enzyme obtained in Example 1.

The methyl vinyl ketone-reducing activity of the enzyme obtained in Example 1 was assayed under standard reaction conditions, with the exception that only the temperatures were altered. The activity is represented by a relative activity, taking the maximal activity as 100, and the results are shown in FIG. 3. The optimal temperature was 37 to 45° C.

EXAMPLE 5

Substrate Specificity of Enone Reductase

The enzyme obtained in Example 1 was reacted with various enones, ketones, and aldehydes, and the dehydrogenation activity was assayed. The result was represented by a relative activity, taking the dehydrogenation activity of the enzyme on methyl vinyl ketone as 100, and the results are shown in Table 2.

TABLE 2

| Substrate | coenzyme | Relative activity (%) |
|---|---|---|
| Methyl vinyl ketone | NADPH | 100 |
| Ethyl vinyl ketone | NADPH | 537 |
| 3-pentene-2-one | NADPH | 16 |
| 4-methyl-3-pentene-2-one | NADPH | 1 |
| 3-methyl-3-pentene-2-one | NADPH | 48 |
| 2-methyl-2-cyclopenten-1-one | NADPH | 0 |
| 3-methyl-2-cyclopenten-1-one | NADPH | 0 |
| 2-butanone | NADPH | 0 |
| Crotonic acid | NADPH | 0 |
| Methylglyoxal | NADPH | 1 |
| 2,3-butanedione | NADPH | 1 |
| Acetophenone | NADPH | 0 |
| Methyl vinyl ketone | NADH | 14 |
| Ethyl vinyl ketone | NADH | 52 |

EXAMPLE 6

Synthesis of 3-pentanone Using Enone Reductase

The reaction was carried out overnight in a reaction solution containing 200 mM potassium phosphate buffer (pH 6.5), 44 mg NADH, 1 U enone reductase, and 0.2% ethyl vinyl ketone at 25° C. The produced 3-pentanone was quantified by gas chromatography, and the yield was determined based on the quantity of the starting material, ethyl vinyl ketone. The condition used for gas chromatography was as follows: Porapak PS (Waters, mesh 50–80, 3.2 mm×210 cm) was used; the column temperature was 130° C.; the analysis was carried out with a flame ionization detector (FID). The result showed that the reaction yield was 100%.

EXAMPLE 7

Partial Amino Acid Sequence of Enone Reductase

The enzyme obtained in Example 1 was fractionated by SDS-PAGE; a gel piece containing the enone reductase was cut out. After washing the gel piece twice, the enzyme was digested overnight in the gel with lysylendopeptidase at 35° C. The digested peptide was fractionated and obtained using reverse HPLC (TSK gel ODS-80-Ts, 2.0 mm×250 mm; Tosoh) by the elution with an acetonitrile gradient in 0.1% trifluoroacetic acid (TFA).

The obtained two peaks of peptide fractions were named lep_64 and lep_65, respectively. Each fraction was analyzed for the amino acid sequence in a protein sequencer (Hewlett Packard G1005A Protein Sequencer System). The amino acid sequences for lep_64 and lep_65 are shown in SEQ ID NOs: 9 and 10, respectively.

SEQ ID NO:9:lep_64
    Ser-Tyr-Gly-Ala-Asp-Asp-Val-Phe-Asp-Tyr-His-Asp

SEQ ID NO:10:lep_65
    Ile-Gly-Pro-Glu-Gly-Ser-Ile-Leu-Gly-Cys-Asp-Ile

EXAMPLE 8

Purification of Chromosomal DNA from *Kluyveromyces lactis*

*Kluyveromyces lactis*, IFO 1267 strain, was cultured in YM culture medium, and the fungal cells were prepared. The purification of chromosomal DNA from the fungal cells was carried out by the method as described in "Meth. Cell Biol. 29, 39–44 (1975)".

EXAMPLE 9

Cloning of the Core Region of Enone Reductase Gene

Three kinds of sense and antisense primers in total were synthesized based on the amino acid sequences of lep_64 and lep_65. Respective nucleotide sequences are shown in SEQ ID NO:11: (KR2-64U), 12 (KR2-65D), and 13 (KR2-65E).

SEQ ID NO:11: KR2-64U
    TGRTARTCRAANACRTCRTC

SEQ ID NO:12: KR2-65D
    ATWGGHCCWGARGGHTCNAT

SEQ ID NO:13: KR2-65E
    ATWGGHCCNGARGGHAGYAT

Two of the three primers were selected as a combination. PCR amplification was conducted with 50 μL reaction solution containing: primers (50 pmol each), 10 nmol dNTP, 50 ng chromosomal DNA derived from *Kluyveromyces lactis*, AmpliTaq buffer (Takara Shuzo), and 2 U AmpliTaq (Takara Shuzo); 30 cycles of denaturation (at 94° C. for 30 seconds), annealing (at 45° C. for 30 seconds), and extension (at 70° C. for 1 minute) on a GeneAmp PCR System 2400 (Perkin Elmer) was carried out.

An aliquot of the PCR reaction solution was analyzed by agarose gel electrophoresis; a band, which was assumed to be specific, was detected from solutions containing KR2–64U and KR2–65D as primers. The obtained DNA fragment was extracted with phenol/chloroform, precipitated by ethanol, and the precipitate was collected. The obtained DNA fragment was ligated to pT7Blue (R) T-vector (Novagen) using the Takara Ligation Kit, and then was transformed into E. coli JM109 strain.

The transformed strain was grown on a plate of LB culture medium (1% bacto-tryptone, 0.5% bacto-yeast extract, 1% sodium chloride; hereinafter abbreviated as LB culture medium) containing ampicillin (50 µg/mL); several white colonies were selected by the blue/white selection method. The length of the inserts in the selected white colonies were checked by colony-direct PCR using commercially available primers M13-21 (TGTAAAACGACGGCCAGT (SEQ ID NO:28)) and M13-RP (CAGGAAACAGCTATGACC (SEQ ID NO:29)). The colonies, which were presumed to contain the DNA fragment of interest as an insert, were cultured in LB liquid culture medium containing ampicillin. The plasmid was purified with Flexi-Prep (Pharmacia), and was named pKLR2.

The nucleotide sequence of the DNA insert was analyzed using the purified plasmid. Nucleotide sequence analysis of the DNA was carried out with a DNA sequencer ABI PRISM™310 (Perkin Elmer), after the DNA was amplified by PCR using the BigDye Terminator Cycle Sequencing FS ready Reaction Kit (Perkin Elmer). The determined nucleotide sequence of the core region is shown in SEQ ID NO:14.

EXAMPLE 10

Nucleotide Sequence Analysis of DNA Regions Adjacent to the Core Region of the Enone Reductase Gene Chromosomal DNA derived from *Kluyveromyces lactis* was digested with the restriction enzyme, HaeII or PstI, and then, was self-ligated overnight at 16° C. using T4 ligase to cyclize each fragment. Then, PCR amplification was conducted in a 50 µL reaction solution containing: primers KL2-5U (SEQ ID NO:15) and KL2-3D (SEQ ID NO:16) (100 pmol each); 25 ng circular DNA; Ex-Taq buffer (Takara Shuzo); and 2 U Ex-Taq (Takara Shuzo). 30 cycles of denaturation (at 94° C. for 30 seconds), annealing (at 55° C. for 30 seconds), and extension (at 72° C. for 7 minutes) on a GeneAmp PCR System 2400 (Perkin Elmer) was carried out. An aliquot of the PCR reaction solution was analyzed by agarose gel electrophoresis; a band of approximately 5000 bp, which was assumed to be specific, was detected. The DNA fragment was purified with a Sephaglas BandPrep Kit (Pharmacia). The nucleotide sequence of the fragment was determined by the primer walking method.

Five kinds of primers were used: KL2-5U, KL2-3D, KL2-Sq1 (SEQ ID NO:17), KL2-Sq2 (SEQ ID NO:18), and KL2-Sq3 (SEQ ID NO:19). Nucleotide sequence analysis of the DNA was carried out by a DNA sequencer ABI PRISM™310 (Perkin Elmer), after the DNA was amplified by PCR using the BigDye Terminator Cycle Sequencing FS ready Reaction Kit (Perkin Elmer). Thus, the ORF sequence of enone reductase was determined. The determined DNA sequence is shown in SEQ ID NO:1; and the sequence of the encoded protein is shown in SEQ ID NO:2. ORF search from the DNA sequence, translation from the ORF to the deduced amino acid sequence, and others, were performed with Genetyx-WIN (Software Development Co., LTD).

SEQ ID NO:15: KL2-5U
TCCGGTACCGACAACTGTACCAGCAATGTC

SEQ ID NO:16: KL2-3D
ATCGGTACCTATACTAAGATTGTAACTGTTGC

SEQ ID NO:17: KL2-Sq1
CCGGGTACCCTTTTAGGGTGA

SEQ ID NO:18: KL2-Sq2
TCATGAAGCCACAGTTAAATTCG

SEQ ID NO:19: KL2-Sq3
ATATTCATATGATGGATATCACCG

EXAMPLE 11

Cloning of the Enone Reductase Gene

Primers for ORF cloning were synthesized based on the sequence of the structural gene of the enone reductase: KLCR2-N (SEQ ID NO:20), and KLCR2-C (SEQ ID NO:21). PCR amplification was conducted in 50 µL reaction solution containing: primers (50 pmol each); 10 nmol dNTP; 50 ng chromosomal DNA derived from *Kluyveromyces lactis*; Pfu Turbo-DNA polymerase buffer (STRATAGENE); and 2.5 U Pfu Turbo-DNA polymerase (STRATAGENE). 30 cycles of denaturation (at 95° C. for 150 seconds), annealing (at 55° C. for 1 minute), and extension (at 75° C. for 90 seconds) on a GeneAmp PCR System 2400 (Perkin Elmer) was carried out.

SEQ ID NO:20: KLCR2-N
CTGGAATTCTACCATGGCTTCAGTTC-CAACCACTCAAAAAG

SEQ ID NO:21: KLCR2-C
GACAAGCTTCTAGATTATAACCTGGCAA-CATACTAACA

An aliquot of the PCR reaction solution was analyzed by agarose gel electrophoresis; a band, which was assumed to be specific, was detected.

The obtained DNA fragment was extracted with phenol/chloroform, precipitated with ethanol, and then, was collected. The DNA fragment was double-digested with restriction enzymes, NcoI and XbaI, and then, was electrophoresed on an agarose gel. The band of interest was cut out, and the DNA was purified with the Sepaglas BandPrep Kit (Pharmacia). The obtained DNA fragment was ligated to pSE420D, which had been double-digested with NcoI and XbaI, using the Takara Ligation Kit. The ligate was transformed into E. coli JM109 strain.

Figure 4:
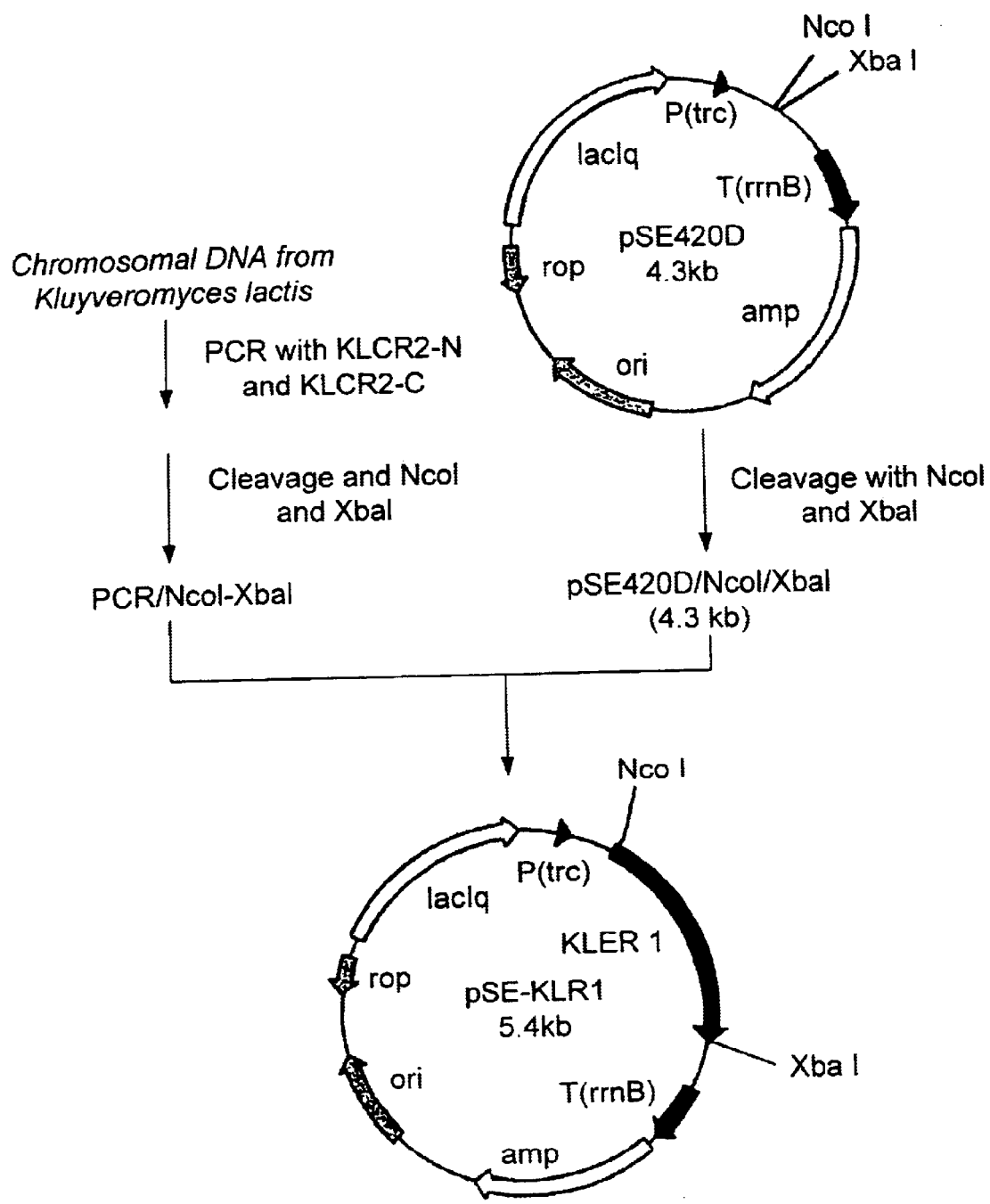
FIG. 4 is a schematic illustration of plasmid pSE-KLR1 containing the enone reductase gene.

The transformed strain was grown on a plate of LB culture medium containing ampicillin (50 µg/mL); and the length of inserts in several colonies were checked by colony-direct PCR using KLCR2-N and KLCR2-C primers. Plasmids were purified from colonies confirmed to contain inserts of the desired size. Then, the nucleotide sequence of the insert fragment was analyzed. The plasmid containing the object enone reductase gene was designated as pSE-KLR1 (FIG. 4).

EXAMPLE 12

Production of Recombinant Enone Reductase in *E. coli*

E. coli HB101 strain, transformed with plasmid pSE-KLR1 expressing the enone reductase, was cultured overnight in liquid LB medium containing ampicillin at 30° C. 0.1 mM IPTG was added to the culture, and then, was further cultured for 4 hours.

The bacterial cells were harvested by centrifugation, and then, were suspended in 50 mM potassium phosphate buffer (pH8.0) containing 0.02% 2-mercaptoethanol, 2mM PMSF, and 10% glycerin. The cells were treated in a closed-chamber sonicator UCD-200TM (Cosmo Bio) for 3 minutes to crush the cells. The bacterial cell lysate was centrifuged and the supernatant was recovered as bacterial cell extract. The extract was assayed for activities to various types of substrates. In addition, E. coli HB 101 strain without the plasmid was cultured overnight in LB culture medium. 0.1 mM IPTG was added to the culture, and then, was further cultured for 4 hours. The bacterial cells were crushed by the same method as above, and the extract was assayed for the activities to various types of substrates. These results are shown in Table 3.

TABLE 3

| Substrate | Host only Specific activity (U/mg) | HB101 (pSE-KLR1) Specific activity (U/mg) | HB101 (pSE-KLR1) Relative activity (%) |
|---|---|---|---|
| Methyl vinyl ketone | 0.066 | 7.78 | 100 |
| Ethyl vinyl ketone | 0.073 | 41.8 | 537 |
| 3-pentene-2-one | 0.015 | 1.23 | 15.9 |
| 3-methyl-3-pentene-2-one | 0.004 | 2.52 | 32.4 |

EXAMPLE 13

Purification of Chromosomal DNA from Saccharomyces cerevisiae

Saccharomyces cerevisiae X2180-1B (Yeast Genetic Stock Center) was cultured in YM culture medium, and the fungal cells were harvested. The purification of chromosomal DNA from the fungal cells was carried out by the method described in "Meth. Cell Biol. 29, 39–44 (1975)".

EXAMPLE 14

Cloning of Enone Reductase Homologue, YNN4

PCR primers, YNN4-ATG1 (SEQ ID NO:22) and YNN-TAA1 (SEQ ID NO:23), were synthesized based on the DNA sequence (DDBJ Accession No. Z46843) corresponding to a putative protein YNN4 (SWISS-PROT Accession No., P53912) deposited in DDBJ.

PCR amplification was conducted in 50 µL reaction solution containing: primers (25 pmol each); 10 nmol dNTP, 50 ng chromosomal DNA derived from Saccharomyces cerevisiae; Pfu DNA polymerase buffer (STRATAGENE); and 2 U Pfu DNA polymerase (STRATAGENE). 30 cycles of denaturation (at 95° C. for 45 seconds), annealing (at 50° C. for 1 minute), and extension (at 75° C. for 6 minutes) on a GeneAmp PCR System 2400 (Perkin Elmer) was carried out. Specific amplification products were provided.

The amplification products were treated with phenol, and then, were double-digested with restriction enzymes, AflIII and XbaI. The resulting fragment was ligated with vector pSE420D, which had been double-digested with restriction enzymes NcoI and XbaI, using the TAKARA Ligation Kit. E. coli JM109 strain was transformed with the ligated DNA, and then, was grown on a plate of LB culture medium containing ampicillin (50 mg/L). Plasmids were purified from the resulting transformant with FlexiPrep. The obtained plasmid was designated as pSE-YNN4.

The nucleotide sequence of the insert DNA in the plasmid was analyzed. The revealed sequence is shown in SEQ ID NO:3. The determined nucleotide sequence perfectly agreed with the nucleotide sequence deposited in DDBJ. The amino acid sequence deduced from the nucleotide sequence of SEQ ID NO:3 is shown in SEQ ID NO:4.

SEQ ID NO:22: YNN4-ATG1
CAAACATGTCTGCCTCGATTCCAGA

SEQ ID NO:23: YNN4-TAA1
CAGTCTAGATTATTTCAAGACGGCAACCAAC

EXAMPLE 15

Cloning of Enone Reductase Homologue, YL60

PCR primers, YL60-ATG2 (SEQ ID NO:24) and YL60-TAA1 (SEQ ID NO:25), were synthesized based on the DNA sequence (DDBJ Accession No. U22383) corresponding to a putative protein YL60 deposited in DDBJ (SWISS-PROT Accession No. P54007).

PCR amplification was conducted in 50 µL reaction solution containing: primers (25 pmol each); 10 nmol dNTP; 50 ng chromosomal DNA derived from Saccharomyces cerevisiae; Pfu DNA polymerase buffer (STRATAGENE); and 2 U Pfu DNA polymerase (STRATAGENE). 30 cycles of denaturation (at 95° C. for 45 seconds), annealing (at 50° C. for 1 minute), and extension (at 75° C. for 6 minutes) on a GeneAmp PCR System 2400 (Perkin Elmer) was carried out. Specific amplification products were provided.

The amplification products were treated with phenol, and then, were double-digested with restriction enzymes, NcoI and XbaI. The resulting fragment was ligated with vector pSE420D, which had been double-digested with restriction enzymes NcoI and XbaI, using the TAKARA Ligation Kit.

E. coli JM109 strain was transformed with the ligated DNA, and then, was grown on a plate of LB culture medium containing ampicillin (50 mg/L). The plasmid was purified from the resulting transformant with FlexiPrep. The obtained plasmid was designated as pSE-YL60.

The nucleotide sequence of the insert DNA in the plasmid was analyzed. The revealed sequence is shown in SEQ ID NO:5. The determined nucleotide sequence perfectly agreed with the nucleotide sequence deposited in DDBJ. The amino acid sequence deduced from the nucleotide sequence of SEQ ID NO:5 is shown in SEQ ID NO:6.

SEQ ID NO:24: YL60-ATG2
CAACCATGGCTCAAGTTGCAATTCCAGAAACC

SEQ ID NO:25: YL60-TAA1
GACTCTAGATTAGTTTAATACGGCAAC-GAGTTTTTCAC

EXAMPLE 16

Cloning of Enone Reductase Homologue, YCZ2

PCR primers, YCZ2-ATG1 (SEQ ID NO:26) and YCZ2-TAA1 (SEQ ID NO:27), were synthesized based on the DNA sequence (DDBJ Accession No. X59720) corresponding to a putative protein YCZ2 deposited in DDBJ (SWISS-PROT Accession No., P25608).

PCR amplification was conducted in 50 µL reaction solution containing: primers (25 pmol each); 10 nmol dNTP; 50 ng chromosomal DNA derived from Saccharomyces cerevisiae; Pfu DNA polymerase buffer (STRATAGENE); and 2U Pfu DNA polymerase (STRATAGENE). 30 cycles of denaturation (at 95° C. for 45 seconds), annealing (at 50° C. for 1 minute), and extension (at 75° C. for 6 minutes) on a GeneAmp PCR System 2400 (Perkin Elmer) was carried out. Specific amplification products were provided.

The amplification products were treated with phenol, and then, were double-digested with restriction enzymes, BspHI and XbaI. The resulting fragment was ligated with vector pSE420D, which had been double-digested with restriction enzymes NcoI and XbaI using the TAKARA Ligation Kit.

E. coli JM109 strain was transformed with the ligated DNA, and then, was grown on a plate of LB culture medium containing ampicillin (50 mg/L). The plasmid was purified from the resulting transformant with FlexiPrep. The plasmid obtained was designated as pSE-YCZ2.

The nucleotide sequence of the insert DNA in the plasmid was analyzed. The revealed sequence is shown in SEQ ID NO:7. While the nucleotide "C" had been substituted for "A" at nucleotide residue 1089 in the determined nucleotide sequence, the sequence of the encoded amino acid was the same as that deposited in the databank. The amino acid sequence deduced from the nucleotide sequence is shown in SEQ ID NO:8.

SEQ ID NO:26: YCZ2-ATG1
GAAATCATGAAAGCTGTCGTCATTGAA

SEQ ID NO:27: YCZ2-TAA1
GTTTCTAGATTAGTTTAATACGGCAACK-AGTTTTTCA

EXAMPLE 17

Verification of the Activity of the Enone Reductase Homologues. YNN4, YL60, and YCZ2

E. coli JM109 strains, each containing pSE-YNN4, pSE-YL60 or pSE-YCZ2, were cultured in LB culture medium containing ampicillin. The induction of the enzyme was achieved by adding 0.1 mM IPTG and culturing for 4 hours. The bacterial cells were harvested by centrifugation. Respective bacterial cells were suspended in cell lysis buffer (50 mM KPB (pH 8.0), 1 mM EDTA, 0.02% 2-ME, 2 mM PMSF, and 10% glycerol); and the cells were lysed in a sonicator. The supernatant prepared by centrifugation was used as the cell-free extract.

Each of the cell-free extract was assayed for the enone reductase activity. The cell-free extracts exhibited activities of 0.268 U/mg protein, 0.198 U/mg protein and 0.133 U/mg protein, respectively. Thus, it was verified that all of the three types of homologues of the enzyme of the present invention had the requisite enone reductase activity.

What is claimed is:

1. An isolated Kluyveromyces lactis reductase wherein the reductase is an enone reductase that:
   (a) reduces the carbon-carbon double bond of an α,β-unsaturated ketone, using NADPH as an electron donor, to produce a corresponding saturated hydrocarbon;
   (b) has an optimal pH of 6.5–7.0;
   (c) has a molecular weight determined by sodium dodecyl sulfate-polyacrylamide gel electrophoresis and by gel filtration of about 43,000 Da and about 42,000 Da, respectively;
   (d) has an optimal temperature within the range of 37–45° C.; and
   (e) has a substrate specificity of (1)–(4):
      (1) substantially no activity to reduce the keto group of a ketone;
      (2) exhibits a significantly higher activity with NADPH than with NADH as an electron donor;
      (3) does not substantially act on a substrate in which neither substituent at the β carbon relative to the ketone is hydrogen; and
      (4) does not substantially act on a substrate in which the carbon-carbon double bond is present in a cyclic structure.

2. An isolated polypeptide the amino acid sequence of which consists of SEQ ID NO:2.

3. An isolated polypeptide the amino acid sequence of which comprises SEQ ID NO:2.

4. A method for selectively reducing the carbon-carbon double bond of an α,β-unsaturated ketone, comprising the step of reacting an α,β-unsaturated ketone with the enone reductase of claim 1.

5. A method for selectively reducing the carbon-carbon double bond of an α,β-unsaturated ketone, comprising the step of reacting an α,β-unsaturated ketone with the polypeptide of claim 2.

6. A method for selectively reducing the carbon-carbon double bond of an α,β-unsaturated ketone, comprising the step of reacting an α,β-unsaturated ketone with the polypeptide of claim 3.

* * * * *

SEQUENCE LISTING

<160> NUMBER OF SEQ ID NOS: 29

<210> SEQ ID NO 1
<211> LENGTH: 1113
<212> TYPE: DNA
<213> ORGANISM: Kluyveromyces lactis
<220> FEATURE:
<221> NAME/KEY: CDS
<222> LOCATION: (1)...(1110)

<400> SEQUENCE: 1

```
atg tca gtt cca acc act caa aaa gcc gtc atc att gaa ggt gac aaa      48
Met Ser Val Pro Thr Thr Gln Lys Ala Val Ile Ile Glu Gly Asp Lys
 1               5                  10                  15 gct gtt gtt aaa aca gat gtc tca gtt cca gaa tta aag gag ggt aca      96
Ala Val Val Lys Thr Asp Val Ser Val Pro Glu Leu Lys Glu Gly Thr
                20                  25                  30 gcc ttg gtg aag gtt gag gct gtt gct ggt aac cca act gat tgg aag     144
Ala Leu Val Lys Val Glu Ala Val Ala Gly Asn Pro Thr Asp Trp Lys
            35                  40                  45 cat att gct tat aag att ggt cca gaa ggt tca att cta gga tgt gac     192
His Ile Ala Tyr Lys Ile Gly Pro Glu Gly Ser Ile Leu Gly Cys Asp
        50                  55                  60 att gct ggt aca gtt gtc aaa ctt gga cca aat gct agt act gac ttg     240
Ile Ala Gly Thr Val Val Lys Leu Gly Pro Asn Ala Ser Thr Asp Leu
    65                  70                  75                  80 aag gtt gga gat acc ggt ttc ggt ttt gtt cac ggt gct tcc caa aca     288
Lys Val Gly Asp Thr Gly Phe Gly Phe Val His Gly Ala Ser Gln Thr
                85                  90                  95 gat cct aaa aat ggt gca ttt gct gaa tat gcc agg gtt tat cca cct     336
Asp Pro Lys Asn Gly Ala Phe Ala Glu Tyr Ala Arg Val Tyr Pro Pro
            100                 105                 110 ttg ttt tac aag agt aac tta act cac tca act gct gat gaa att tct     384
Leu Phe Tyr Lys Ser Asn Leu Thr His Ser Thr Ala Asp Glu Ile Ser
        115                 120                 125 gaa ggc cct gtg aag aac ttc gaa tct gct gca tca ttg cca gtt tcg     432
```

|  |  |  |  |  |  |  |  |  |  |  |  |  |  |  |  |
|---|---|---|---|---|---|---|---|---|---|---|---|---|---|---|---|
| Glu | Gly | Pro | Val | Lys | Asn | Phe | Glu | Ser | Ala | Ala | Ser | Leu | Pro | Val | Ser |
|  | 130 |  |  |  | 135 |  |  |  | 140 |  |  |  |  |  |  |

```
ttg aca act gct ggt gtt agt ttg tgt cat cac ttg ggc tca aaa atg      480
Leu Thr Thr Ala Gly Val Ser Leu Cys His His Leu Gly Ser Lys Met
145             150                 155                 160 gaa tgg cac cca tct acc ccg caa cat act cat cca tta ttg att tgg      528
Glu Trp His Pro Ser Thr Pro Gln His Thr His Pro Leu Leu Ile Trp
            165                 170                 175 ggt ggt gct aca gca gtg ggt caa caa cta atc caa gtt gcc aaa cat      576
Gly Gly Ala Thr Ala Val Gly Gln Gln Leu Ile Gln Val Ala Lys His
            180                 185                 190 atc aat gct tat act aag att gta act gtt gct tct aaa aag cat gaa      624
Ile Asn Ala Tyr Thr Lys Ile Val Thr Val Ala Ser Lys Lys His Glu
        195                 200                 205 aag ctt tta aag tct tat ggt gct gat gat gtc ttt gac tat cat gat      672
Lys Leu Leu Lys Ser Tyr Gly Ala Asp Asp Val Phe Asp Tyr His Asp
    210                 215                 220 gca ggc gtt att gag cag atc aaa tcg aag tat cca aac ctg caa cat      720
Ala Gly Val Ile Glu Gln Ile Lys Ser Lys Tyr Pro Asn Leu Gln His
225                 230                 235                 240 gtt att gac gct gtg gga agc gaa gat agt atc ccc gag gcc tat aaa      768
Val Ile Asp Ala Val Gly Ser Glu Asp Ser Ile Pro Glu Ala Tyr Lys
                245                 250                 255 gtc aca gca gat agt cta cct gcc aca tta tta gaa gtg gtt cca atg      816
Val Thr Ala Asp Ser Leu Pro Ala Thr Leu Leu Glu Val Val Pro Met
            260                 265                 270 acc att gaa agc att cct gaa gaa atc aga aaa gat aat gtt aaa att      864
Thr Ile Glu Ser Ile Pro Glu Glu Ile Arg Lys Asp Asn Val Lys Ile
            275                 280                 285 gat att act ttg ttg tat cgt gca tct ggt caa gaa att cta ttg ggt      912
Asp Ile Thr Leu Leu Tyr Arg Ala Ser Gly Gln Glu Ile Leu Leu Gly
    290                 295                 300 gca aca aga ttt cct gct agt cca gaa tat cat gaa gcc aca gtt aaa      960
Ala Thr Arg Phe Pro Ala Ser Pro Glu Tyr His Glu Ala Thr Val Lys
305                 310                 315                 320 ttc gtt aag ttt ata aat cca cac ctt aac aac ggt gat atc cat cat     1008
Phe Val Lys Phe Ile Asn Pro His Leu Asn Asn Gly Asp Ile His His
                325                 330                 335 atg aat att aaa gtt ttc agc aac ggc tta gat gat gtc cca gct ctc     1056
Met Asn Ile Lys Val Phe Ser Asn Gly Leu Asp Asp Val Pro Ala Leu
            340                 345                 350 act gaa ggt ata aaa gaa ggt aaa aac aaa aat gtt aag tat gtt gcc     1104
Thr Glu Gly Ile Lys Glu Gly Lys Asn Lys Asn Val Lys Tyr Val Ala
            355                 360                 365 agg tta taa                                                         1113
Arg Leu
    370

<210> SEQ ID NO 2
<211> LENGTH: 370
<212> TYPE: PRT
<213> ORGANISM: Kluyveromyces lactis

<400> SEQUENCE: 2

Met Ser Val Pro Thr Thr Gln Lys Ala Val Ile Ile Glu Gly Asp Lys
  1               5                  10                  15

Ala Val Val Lys Thr Asp Val Ser Val Pro Glu Leu Lys Glu Gly Thr
             20                  25                  30

Ala Leu Val Lys Val Glu Ala Val Ala Gly Asn Pro Thr Asp Trp Lys
         35                  40                  45
```

```
His Ile Ala Tyr Lys Ile Gly Pro Glu Gly Ser Ile Leu Gly Cys Asp
     50                  55                  60

Ile Ala Gly Thr Val Val Lys Leu Gly Pro Asn Ala Ser Thr Asp Leu
 65                  70                  75                  80

Lys Val Gly Asp Thr Gly Phe Gly Phe Val His Gly Ala Ser Gln Thr
                 85                  90                  95

Asp Pro Lys Asn Gly Ala Phe Ala Glu Tyr Ala Arg Val Tyr Pro Pro
            100                 105                 110

Leu Phe Tyr Lys Ser Asn Leu Thr His Ser Thr Ala Asp Glu Ile Ser
            115                 120                 125

Glu Gly Pro Val Lys Asn Phe Glu Ser Ala Ala Ser Leu Pro Val Ser
        130                 135                 140

Leu Thr Thr Ala Gly Val Ser Leu Cys His His Leu Gly Ser Lys Met
145                 150                 155                 160

Glu Trp His Pro Ser Thr Pro Gln His Thr His Pro Leu Leu Ile Trp
                165                 170                 175

Gly Gly Ala Thr Ala Val Gly Gln Gln Leu Ile Gln Val Ala Lys His
            180                 185                 190

Ile Asn Ala Tyr Thr Lys Ile Val Thr Val Ala Ser Lys Lys His Glu
        195                 200                 205

Lys Leu Leu Lys Ser Tyr Gly Ala Asp Asp Val Phe Asp Tyr His Asp
210                 215                 220

Ala Gly Val Ile Glu Gln Ile Lys Ser Lys Tyr Pro Asn Leu Gln His
225                 230                 235                 240

Val Ile Asp Ala Val Gly Ser Glu Asp Ser Ile Pro Glu Ala Tyr Lys
                245                 250                 255

Val Thr Ala Asp Ser Leu Pro Ala Thr Leu Leu Glu Val Val Pro Met
            260                 265                 270

Thr Ile Glu Ser Ile Pro Glu Glu Ile Arg Lys Asp Asn Val Lys Ile
        275                 280                 285

Asp Ile Thr Leu Leu Tyr Arg Ala Ser Gly Gln Glu Ile Leu Leu Gly
290                 295                 300

Ala Thr Arg Phe Pro Ala Ser Pro Glu Tyr His Glu Ala Thr Val Lys
305                 310                 315                 320

Phe Val Lys Phe Ile Asn Pro His Leu Asn Asn Gly Asp Ile His His
                325                 330                 335

Met Asn Ile Lys Val Phe Ser Asn Gly Leu Asp Asp Val Pro Ala Leu
            340                 345                 350

Thr Glu Gly Ile Lys Glu Gly Lys Asn Lys Asn Val Lys Tyr Val Ala
        355                 360                 365

Arg Leu
    370

<210> SEQ ID NO 3
<211> LENGTH: 1145
<212> TYPE: DNA
<213> ORGANISM: Saccharomyces cerevisiae
<220> FEATURE:
<221> NAME/KEY: CDS
<222> LOCATION: (6)...(1133)

<400> SEQUENCE: 3 caaac atg tct gcc tcg att cca gaa acc atg aaa gcc gtt gtc att gaa      50
      Met Ser Ala Ser Ile Pro Glu Thr Met Lys Ala Val Val Ile Glu
       1               5                  10                  15
```

-continued

| | |
|---|---|
| aat ggc aag gct gta gtc aaa cag gac att cca att cct gaa tta gaa<br>Asn Gly Lys Ala Val Val Lys Gln Asp Ile Pro Ile Pro Glu Leu Glu<br>             20                          25                 30 | 98 |
| gaa gga ttt gtt cta att aag act gtc gcc gtt gcc ggt aac cct acc<br>Glu Gly Phe Val Leu Ile Lys Thr Val Ala Val Ala Gly Asn Pro Thr<br>         35                      40                       45 | 146 |
| gat tgg aaa cat att gat ttc aag att ggt cct caa ggt gcc ctc tta<br>Asp Trp Lys His Ile Asp Phe Lys Ile Gly Pro Gln Gly Ala Leu Leu<br>        50                      55                    60 | 194 |
| ggc tgt gat gca gcc ggc caa atc gta aag ttg ggc cca aat gtt gat<br>Gly Cys Asp Ala Ala Gly Gln Ile Val Lys Leu Gly Pro Asn Val Asp<br>65                    70                    75 | 242 |
| gct gca cgc ttt gcc att ggt gat tac att tat ggg gtt att cac ggt<br>Ala Ala Arg Phe Ala Ile Gly Asp Tyr Ile Tyr Gly Val Ile His Gly<br>80                     85                    90                    95 | 290 |
| gct tca gtg agg ttc ccc tca aac ggt gcc ttt gct gag tac tct gcc<br>Ala Ser Val Arg Phe Pro Ser Asn Gly Ala Phe Ala Glu Tyr Ser Ala<br>                   100                   105                110 | 338 |
| att tca tcc gag act gct tat aaa cca gcc aga gag ttt aga ttg tgc<br>Ile Ser Ser Glu Thr Ala Tyr Lys Pro Ala Arg Glu Phe Arg Leu Cys<br>              115                    120                  125 | 386 |
| ggt aaa gac aag cta cca gaa ggc ccc gta aaa tct tta gaa ggg gca<br>Gly Lys Asp Lys Leu Pro Glu Gly Pro Val Lys Ser Leu Glu Gly Ala<br>        130                    135                  140 | 434 |
| gta tcc ctc cca gtc tca ttg acc acg gct ggt atg atc ctt aca cat<br>Val Ser Leu Pro Val Ser Leu Thr Thr Ala Gly Met Ile Leu Thr His<br>145                   150                    155 | 482 |
| agt ttt ggc ttg gac atg aca tgg aag ccc tcc aaa gcg caa aga gat<br>Ser Phe Gly Leu Asp Met Thr Trp Lys Pro Ser Lys Ala Gln Arg Asp<br>160                   165                    170                  175 | 530 |
| caa ccc atc tta ttt tgg ggt ggt gcc act gct gtt ggc cag atg ctt<br>Gln Pro Ile Leu Phe Trp Gly Gly Ala Thr Ala Val Gly Gln Met Leu<br>                  180                    185                  190 | 578 |
| att caa ttg gca aaa aaa cta aac ggt ttc agc aag atc atc gtc gtt<br>Ile Gln Leu Ala Lys Lys Leu Asn Gly Phe Ser Lys Ile Ile Val Val<br>        195                    200                  205 | 626 |
| gct tct cgt aaa cat gaa aaa ttg ttg aaa gag tac ggt gca gat gaa<br>Ala Ser Arg Lys His Glu Lys Leu Leu Lys Glu Tyr Gly Ala Asp Glu<br>          210                    215                  220 | 674 |
| ctt ttt gac tac cac gat gct gac gtt atc gaa cag ata aaa aag aag<br>Leu Phe Asp Tyr His Asp Ala Asp Val Ile Glu Gln Ile Lys Lys Lys<br>225                   230                    235 | 722 |
| tac aac aac att cct tac ttg gtg gac tgt gtc tcc aac aca gaa act<br>Tyr Asn Asn Ile Pro Tyr Leu Val Asp Cys Val Ser Asn Thr Glu Thr<br>240                   245                    250                  255 | 770 |
| att caa cag gtg tac aaa tgt gcc gct gat gac tta gac gct acg gtc<br>Ile Gln Gln Val Tyr Lys Cys Ala Ala Asp Asp Leu Asp Ala Thr Val<br>                  260                    265                  270 | 818 |
| gtt caa ttg acc gtt tta acc gaa aaa gat atc aag gag gaa gac agg<br>Val Gln Leu Thr Val Leu Thr Glu Lys Asp Ile Lys Glu Glu Asp Arg<br>        275                    280                  285 | 866 |
| agg caa aac gtc agt att gaa gga acc ctt cta tat ttg ata gga ggt<br>Arg Gln Asn Val Ser Ile Glu Gly Thr Leu Leu Tyr Leu Ile Gly Gly<br>          290                    295                  300 | 914 |
| aac gac gtc cca ttt ggc acg ttt act ttg cca gca gac cct gaa tac<br>Asn Asp Val Pro Phe Gly Thr Phe Thr Leu Pro Ala Asp Pro Glu Tyr<br>305                   310                    315 | 962 |
| aag gaa gcc gcc ata aaa ttt att aag ttc atc aat cca aaa atc aat<br>Lys Glu Ala Ala Ile Lys Phe Ile Lys Phe Ile Asn Pro Lys Ile Asn<br>320                   325                    330                  335 | 1010 |

```
gat ggt gaa atc cac cac atc cca gtg aaa gtt tac aag aac ggg tta      1058
Asp Gly Glu Ile His His Ile Pro Val Lys Val Tyr Lys Asn Gly Leu
                340                 345                 350 gat gat atc cca cag tta ctt gat gat att aag cac ggg agg aat tct      1106
Asp Asp Ile Pro Gln Leu Leu Asp Asp Ile Lys His Gly Arg Asn Ser
                355                 360                 365 ggc gaa aag ttg gtt gcc gtc ttg aaa taatctagac tg                    1145
Gly Glu Lys Leu Val Ala Val Leu Lys
                370                 375

<210> SEQ ID NO 4
<211> LENGTH: 376
<212> TYPE: PRT
<213> ORGANISM: Saccharomyces cerevisiae

<400> SEQUENCE: 4

Met Ser Ala Ser Ile Pro Glu Thr Met Lys Ala Val Val Ile Glu Asn
 1               5                  10                  15

Gly Lys Ala Val Val Lys Gln Asp Ile Pro Ile Pro Glu Leu Glu Glu
                20                  25                  30

Gly Phe Val Leu Ile Lys Thr Val Ala Val Ala Gly Asn Pro Thr Asp
                35                  40                  45

Trp Lys His Ile Asp Phe Lys Ile Gly Pro Gln Gly Ala Leu Leu Gly
            50                  55                  60

Cys Asp Ala Ala Gly Gln Ile Val Lys Leu Gly Pro Asn Val Asp Ala
 65                  70                  75                  80

Ala Arg Phe Ala Ile Gly Asp Tyr Ile Tyr Gly Val Ile His Gly Ala
                85                  90                  95

Ser Val Arg Phe Pro Ser Asn Gly Ala Phe Ala Glu Tyr Ser Ala Ile
                100                 105                 110

Ser Ser Glu Thr Ala Tyr Lys Pro Ala Arg Glu Phe Arg Leu Cys Gly
            115                 120                 125

Lys Asp Lys Leu Pro Glu Gly Pro Val Lys Ser Leu Glu Gly Ala Val
130                 135                 140

Ser Leu Pro Val Ser Leu Thr Thr Ala Gly Met Ile Leu Thr His Ser
145                 150                 155                 160

Phe Gly Leu Asp Met Thr Trp Lys Pro Ser Lys Ala Gln Arg Asp Gln
                165                 170                 175

Pro Ile Leu Phe Trp Gly Gly Ala Thr Ala Val Gly Gln Met Leu Ile
                180                 185                 190

Gln Leu Ala Lys Lys Leu Asn Gly Phe Ser Lys Ile Ile Val Val Ala
            195                 200                 205

Ser Arg Lys His Glu Lys Leu Leu Lys Glu Tyr Gly Ala Asp Glu Leu
210                 215                 220

Phe Asp Tyr His Asp Ala Asp Val Ile Glu Gln Ile Lys Lys Lys Tyr
225                 230                 235                 240

Asn Asn Ile Pro Tyr Leu Val Asp Cys Val Ser Asn Thr Glu Thr Ile
                245                 250                 255

Gln Gln Val Tyr Lys Cys Ala Ala Asp Asp Leu Asp Ala Thr Val Val
                260                 265                 270

Gln Leu Thr Val Leu Thr Glu Lys Asp Ile Lys Glu Glu Asp Arg Arg
            275                 280                 285

Gln Asn Val Ser Ile Glu Gly Thr Leu Leu Tyr Leu Ile Gly Gly Asn
290                 295                 300

Asp Val Pro Phe Gly Thr Phe Thr Leu Pro Ala Asp Pro Glu Tyr Lys
```

-continued

```
                305                 310                 315                 320
    Glu Ala Ala Ile Lys Phe Ile Lys Phe Ile Asn Pro Lys Ile Asn Asp
                        325                 330                 335

Gly Glu Ile His His Ile Pro Val Lys Val Tyr Lys Asn Gly Leu Asp
                    340                 345                 350

Asp Ile Pro Gln Leu Leu Asp Asp Ile Lys His Gly Arg Asn Ser Gly
                355                 360                 365

Glu Lys Leu Val Ala Val Leu Lys
            370                 375

<210> SEQ ID NO 5
<211> LENGTH: 1134
<212> TYPE: DNA
<213> ORGANISM: Saccharomyces cerevisiae
<220> FEATURE:
<221> NAME/KEY: CDS
<222> LOCATION: (1)...(1131)

<400> SEQUENCE: 5 atg gct caa gtt gca att cca gaa acc atg aag gct gtc gtc att gaa     48
Met Ala Gln Val Ala Ile Pro Glu Thr Met Lys Ala Val Val Ile Glu
 1               5                  10                  15 gac ggt aaa gcg gtt gtt aaa gag ggc att ccc att cct gaa ttg gaa     96
Asp Gly Lys Ala Val Val Lys Glu Gly Ile Pro Ile Pro Glu Leu Glu
                20                  25                  30 gaa gga ttc gta ttg att aag aca ctc gct gtt gct ggt aac ccc act    144
Glu Gly Phe Val Leu Ile Lys Thr Leu Ala Val Ala Gly Asn Pro Thr
            35                  40                  45 gat tgg gca cac att gac tac aag atc ggg cct caa gga tct att ctg    192
Asp Trp Ala His Ile Asp Tyr Lys Ile Gly Pro Gln Gly Ser Ile Leu
        50                  55                  60 gga tgt gat gct gct ggc caa att gtc aaa ttg ggc cca gct gtc aat    240
Gly Cys Asp Ala Ala Gly Gln Ile Val Lys Leu Gly Pro Ala Val Asn
 65                  70                  75                  80 cct aaa gac ttt tct atc ggt gat tat att tat ggg ttc att cac gga    288
Pro Lys Asp Phe Ser Ile Gly Asp Tyr Ile Tyr Gly Phe Ile His Gly
                 85                  90                  95 tct tcc gta agg ttt cct tcc aat ggt gct ttt gct gaa tat tct gct    336
Ser Ser Val Arg Phe Pro Ser Asn Gly Ala Phe Ala Glu Tyr Ser Ala
               100                 105                 110 att tca act gtg gtt gcc tac aaa tca ccc aat gaa ctc aaa ttt ttg    384
Ile Ser Thr Val Val Ala Tyr Lys Ser Pro Asn Glu Leu Lys Phe Leu
           115                 120                 125 ggt gag gat gtt cta cct gcc ggc cct gtc agg tct ttg gaa ggt gta    432
Gly Glu Asp Val Leu Pro Ala Gly Pro Val Arg Ser Leu Glu Gly Val
       130                 135                 140 gcc act atc cca gtg tca ctg acc aca gcc ggc ttg gtg ttg acc tat    480
Ala Thr Ile Pro Val Ser Leu Thr Thr Ala Gly Leu Val Leu Thr Tyr
145                 150                 155                 160 aac ttg ggc ttg gac ctg aag tgg gag cca tca acc cca caa aga aaa    528
Asn Leu Gly Leu Asp Leu Lys Trp Glu Pro Ser Thr Pro Gln Arg Lys
                165                 170                 175 ggc ccc atc tta tta tgg ggc ggt gca act gca gta ggt cag tcg ctc    576
Gly Pro Ile Leu Leu Trp Gly Gly Ala Thr Ala Val Gly Gln Ser Leu
            180                 185                 190 atc caa tta gcc aat aaa ttg aat ggc ttc acc aag atc att gtt gtg    624
Ile Gln Leu Ala Asn Lys Leu Asn Gly Phe Thr Lys Ile Ile Val Val
        195                 200                 205 gct tct cgg aag cac gaa aaa ctt ttg aaa gaa tat ggt gct gat gaa    672
Ala Ser Arg Lys His Glu Lys Leu Leu Lys Glu Tyr Gly Ala Asp Glu
```

```
                     210                 215                 220
tta ttt gat tat cat gat att gac gtg gta gaa caa att aaa cac aag      720
Leu Phe Asp Tyr His Asp Ile Asp Val Val Glu Gln Ile Lys His Lys
225                 230                 235                 240 tac aac aat atc tcg tat tta gtc gac tgt gtc gcg aat caa gat acg      768
Tyr Asn Asn Ile Ser Tyr Leu Val Asp Cys Val Ala Asn Gln Asp Thr
                    245                 250                 255 ctt caa caa gtg tac aaa tgt gcg gcc gat aaa cag gat gct aca att      816
Leu Gln Gln Val Tyr Lys Cys Ala Ala Asp Lys Gln Asp Ala Thr Ile
                260                 265                 270 gtt gaa tta aaa aat ttg aca gaa gaa aac gtc aaa aaa gag aac agg      864
Val Glu Leu Lys Asn Leu Thr Glu Glu Asn Val Lys Lys Glu Asn Arg
            275                 280                 285 aga caa aac gtt act att gac ata ata agg cta tat tca ata ggt ggc      912
Arg Gln Asn Val Thr Ile Asp Ile Ile Arg Leu Tyr Ser Ile Gly Gly
        290                 295                 300 cat gaa gta cca ttt gga aac att act tta cca gcc gac tca gaa gct      960
His Glu Val Pro Phe Gly Asn Ile Thr Leu Pro Ala Asp Ser Glu Ala
305                 310                 315                 320 agg aaa gct gca ata aaa ttt atc aaa ttc atc aat cca aag att aat     1008
Arg Lys Ala Ala Ile Lys Phe Ile Lys Phe Ile Asn Pro Lys Ile Asn
                325                 330                 335 gat gga caa att cgc cat att cca gta agg gtc tat aag aac ggg ctt     1056
Asp Gly Gln Ile Arg His Ile Pro Val Arg Val Tyr Lys Asn Gly Leu
            340                 345                 350 tgt gat gtt cct cat atc cta aaa gac atc aaa tat ggt aag aac tct     1104
Cys Asp Val Pro His Ile Leu Lys Asp Ile Lys Tyr Gly Lys Asn Ser
        355                 360                 365 ggt gaa aaa ctc gtt gcc gta tta aac taa                              1134
Gly Glu Lys Leu Val Ala Val Leu Asn
    370                 375

<210> SEQ ID NO 6
<211> LENGTH: 377
<212> TYPE: PRT
<213> ORGANISM: Saccharomyces cerevisiae

<400> SEQUENCE: 6

Met Ala Gln Val Ala Ile Pro Glu Thr Met Lys Ala Val Val Ile Glu
1               5                   10                  15

Asp Gly Lys Ala Val Val Lys Glu Gly Ile Pro Ile Pro Glu Leu Glu
            20                  25                  30

Glu Gly Phe Val Leu Ile Lys Thr Leu Ala Val Ala Gly Asn Pro Thr
        35                  40                  45

Asp Trp Ala His Ile Asp Tyr Lys Ile Gly Pro Gln Gly Ser Ile Leu
    50                  55                  60

Gly Cys Asp Ala Ala Gly Gln Ile Val Lys Leu Gly Pro Ala Val Asn
65                  70                  75                  80

Pro Lys Asp Phe Ser Ile Gly Asp Tyr Ile Tyr Gly Phe Ile His Gly
                85                  90                  95

Ser Ser Val Arg Phe Pro Ser Asn Gly Ala Phe Ala Glu Tyr Ser Ala
            100                 105                 110

Ile Ser Thr Val Val Ala Tyr Lys Ser Pro Asn Glu Leu Lys Phe Leu
        115                 120                 125

Gly Glu Asp Val Leu Pro Ala Gly Pro Val Arg Ser Leu Glu Gly Val
    130                 135                 140

Ala Thr Ile Pro Val Ser Leu Thr Thr Ala Gly Leu Val Leu Thr Tyr
145                 150                 155                 160
```

-continued

```
Asn Leu Gly Leu Asp Leu Lys Trp Glu Pro Ser Thr Pro Gln Arg Lys
            165                 170                 175
Gly Pro Ile Leu Leu Trp Gly Gly Ala Thr Ala Val Gly Gln Ser Leu
        180                 185                 190
Ile Gln Leu Ala Asn Lys Leu Asn Gly Phe Thr Lys Ile Ile Val Val
    195                 200                 205
Ala Ser Arg Lys His Glu Lys Leu Leu Lys Glu Tyr Gly Ala Asp Glu
210                 215                 220
Leu Phe Asp Tyr His Asp Ile Asp Val Val Glu Gln Ile Lys His Lys
225                 230                 235                 240
Tyr Asn Asn Ile Ser Tyr Leu Val Asp Cys Val Ala Asn Gln Asp Thr
                245                 250                 255
Leu Gln Gln Val Tyr Lys Cys Ala Ala Asp Lys Gln Asp Ala Thr Ile
            260                 265                 270
Val Glu Leu Lys Asn Leu Thr Glu Glu Asn Val Lys Lys Glu Asn Arg
        275                 280                 285
Arg Gln Asn Val Thr Ile Asp Ile Ile Arg Leu Tyr Ser Ile Gly Gly
    290                 295                 300
His Glu Val Pro Phe Gly Asn Ile Thr Leu Pro Ala Asp Ser Glu Ala
305                 310                 315                 320
Arg Lys Ala Ala Ile Lys Phe Ile Lys Phe Ile Asn Pro Lys Ile Asn
                325                 330                 335
Asp Gly Gln Ile Arg His Ile Pro Val Arg Val Tyr Lys Asn Gly Leu
            340                 345                 350
Cys Asp Val Pro His Ile Leu Lys Asp Ile Lys Tyr Gly Lys Asn Ser
        355                 360                 365
Gly Glu Lys Leu Val Ala Val Leu Asn
    370                 375

<210> SEQ ID NO 7
<211> LENGTH: 1122
<212> TYPE: DNA
<213> ORGANISM: Saccharomyces cerevisiae
<220> FEATURE:
<221> NAME/KEY: CDS
<222> LOCATION: (7)...(1110)

<400> SEQUENCE: 7 gaaatc atg aaa gct gtc gtc att gaa gac ggt aaa gcg gtt gtc aaa      48
       Met Lys Ala Val Val Ile Glu Asp Gly Lys Ala Val Val Lys
         1               5                  10 gag ggc gtt ccc att cct gaa ttg gaa gaa gga ttc gta ttg att aag    96
Glu Gly Val Pro Ile Pro Glu Leu Glu Glu Gly Phe Val Leu Ile Lys
 15                  20                  25                  30 aca ctc gct gtt gct ggt aac ccg act gat tgg gca cac att gac tac   144
Thr Leu Ala Val Ala Gly Asn Pro Thr Asp Trp Ala His Ile Asp Tyr
                 35                  40                  45 aag gtc ggg cct caa gga tct att ctg gga tgt gac gct gcc ggc caa   192
Lys Val Gly Pro Gln Gly Ser Ile Leu Gly Cys Asp Ala Ala Gly Gln
             50                  55                  60 att gtc aaa ttg ggc cca gcc gtc gat cct aaa gac ttt tct att ggt   240
Ile Val Lys Leu Gly Pro Ala Val Asp Pro Lys Asp Phe Ser Ile Gly
         65                  70                  75 gat tat att tat ggg ttc att cac gga tct tcc gta agg ttt cct tcc   288
Asp Tyr Ile Tyr Gly Phe Ile His Gly Ser Ser Val Arg Phe Pro Ser
     80                  85                  90 aat ggt gct ttt gct gaa tat tct gct att tca act gtg gtt gcc tac   336
```

```

Asn Gly Ala Phe Ala Glu Tyr Ser Ala Ile Ser Thr Val Val Ala Tyr
 95                 100                 105                 110 aaa tca ccc aat gaa ctc aaa ttt ttg ggt gaa gat gtt cta cct gcc       384
Lys Ser Pro Asn Glu Leu Lys Phe Leu Gly Glu Asp Val Leu Pro Ala
                115                 120                 125 ggc cct gtc agg tct ttg gaa ggg gca gcc act atc cca gtg tca ctg       432
Gly Pro Val Arg Ser Leu Glu Gly Ala Ala Thr Ile Pro Val Ser Leu
            130                 135                 140 acc aca gct ggc ttg gtg ttg acc tat aac ttg ggt ttg aac ctg aag       480
Thr Thr Ala Gly Leu Val Leu Thr Tyr Asn Leu Gly Leu Asn Leu Lys
                145                 150                 155 tgg gag cca tca acc cca caa aga aac ggc ccc atc tta tta tgg ggc       528
Trp Glu Pro Ser Thr Pro Gln Arg Asn Gly Pro Ile Leu Leu Trp Gly
        160                 165                 170 ggt gca act gca gta ggt cag tcg ctc atc caa tta gcc aat aaa ttg       576
Gly Ala Thr Ala Val Gly Gln Ser Leu Ile Gln Leu Ala Asn Lys Leu
175                 180                 185                 190 aat ggc ttc acc aag atc att gtt gtg gct tct cgg aaa cac gaa aaa       624
Asn Gly Phe Thr Lys Ile Ile Val Val Ala Ser Arg Lys His Glu Lys
                195                 200                 205 ctg ttg aaa gaa tat ggt gct gat caa cta ttt gat tac cat gat att       672
Leu Leu Lys Glu Tyr Gly Ala Asp Gln Leu Phe Asp Tyr His Asp Ile
            210                 215                 220 gac gtg gta gaa caa att aaa cac aag tac aac aat atc tcg tat tta       720
Asp Val Val Glu Gln Ile Lys His Lys Tyr Asn Asn Ile Ser Tyr Leu
        225                 230                 235 gtc gac tgt gtc gcg aat caa aat acg ctt caa caa gtg tac aaa tgt       768
Val Asp Cys Val Ala Asn Gln Asn Thr Leu Gln Gln Val Tyr Lys Cys
240                 245                 250 gcg gcc gat aaa cag gat gct acc gtt gtc gaa tta act aat ttg aca       816
Ala Ala Asp Lys Gln Asp Ala Thr Val Val Glu Leu Thr Asn Leu Thr
255                 260                 265                 270 gaa gaa aac gtc aaa aag gag aat agg agg caa aat gtc act att gac       864
Glu Glu Asn Val Lys Lys Glu Asn Arg Arg Gln Asn Val Thr Ile Asp
                275                 280                 285 aga aca aga ctg tat tca ata ggc ggc cat gaa gta cca ttt ggt ggc       912
Arg Thr Arg Leu Tyr Ser Ile Gly Gly His Glu Val Pro Phe Gly Gly
            290                 295                 300 att act ttc cct gct gac cca gaa gcc agg aga gct gcc acc gaa ttc       960
Ile Thr Phe Pro Ala Asp Pro Glu Ala Arg Arg Ala Ala Thr Glu Phe
        305                 310                 315 gtc aag ttc atc aat cca aag att agt gat ggg caa att cac cat att      1008
Val Lys Phe Ile Asn Pro Lys Ile Ser Asp Gly Gln Ile His His Ile
320                 325                 330 cca gca agg gtc tat aag aac ggg ctt tac gat gtt cct cgt atc ctg      1056
Pro Ala Arg Val Tyr Lys Asn Gly Leu Tyr Asp Val Pro Arg Ile Leu
335                 340                 345                 350 gaa gac att aaa atc ggt aag aac tct ggt gaa aaa ctc gtt gcc gta      1104
Glu Asp Ile Lys Ile Gly Lys Asn Ser Gly Glu Lys Leu Val Ala Val
                355                 360                 365 tta aac taatctagaa ac                                                 1122
Leu Asn <210> SEQ ID NO 8
<211> LENGTH: 368
<212> TYPE: PRT
<213> ORGANISM: Saccharomyces cerevisiae

<400> SEQUENCE: 8

Met Lys Ala Val Val Ile Glu Asp Gly Lys Ala Val Val Lys Glu Gly
```

-continued

```
  1               5                  10                 15
Val Pro Ile Pro Glu Leu Glu Gly Phe Val Leu Ile Lys Thr Leu
                 20                 25                 30
Ala Val Ala Gly Asn Pro Thr Asp Trp Ala His Ile Asp Tyr Lys Val
                 35                 40                 45
Gly Pro Gln Gly Ser Ile Leu Gly Cys Asp Ala Ala Gly Gln Ile Val
                 50                 55                 60
Lys Leu Gly Pro Ala Val Asp Pro Lys Asp Phe Ser Ile Gly Asp Tyr
 65                 70                 75                 80
Ile Tyr Gly Phe Ile His Gly Ser Ser Val Arg Phe Pro Ser Asn Gly
                    85                 90                 95
Ala Phe Ala Glu Tyr Ser Ala Ile Ser Thr Val Ala Tyr Lys Ser
                   100                105                110
Pro Asn Glu Leu Lys Phe Leu Gly Glu Asp Val Leu Pro Ala Gly Pro
                   115                120                125
Val Arg Ser Leu Glu Gly Ala Ala Thr Ile Pro Val Ser Leu Thr Thr
                   130                135                140
Ala Gly Leu Val Leu Thr Tyr Asn Leu Gly Leu Asn Leu Lys Trp Glu
145                    150                155                160
Pro Ser Thr Pro Gln Arg Asn Gly Pro Ile Leu Leu Trp Gly Gly Ala
                       165                170                175
Thr Ala Val Gly Gln Ser Leu Ile Gln Leu Ala Asn Lys Leu Asn Gly
                   180                185                190
Phe Thr Lys Ile Ile Val Val Ala Ser Arg Lys His Glu Lys Leu Leu
                   195                200                205
Lys Glu Tyr Gly Ala Asp Gln Leu Phe Asp Tyr His Asp Ile Asp Val
                   210                215                220
Val Glu Gln Ile Lys His Lys Tyr Asn Asn Ile Ser Tyr Leu Val Asp
225                    230                235                240
Cys Val Ala Asn Gln Asn Thr Leu Gln Gln Val Tyr Lys Cys Ala Ala
                       245                250                255
Asp Lys Gln Asp Ala Thr Val Val Glu Leu Thr Asn Leu Thr Glu Glu
                   260                265                270
Asn Val Lys Lys Glu Asn Arg Arg Gln Asn Val Thr Ile Asp Arg Thr
                   275                280                285
Arg Leu Tyr Ser Ile Gly Gly His Glu Val Pro Phe Gly Gly Ile Thr
                   290                295                300
Phe Pro Ala Asp Pro Glu Ala Arg Arg Ala Ala Thr Glu Phe Val Lys
305                    310                315                320
Phe Ile Asn Pro Lys Ile Ser Asp Gly Gln Ile His His Ile Pro Ala
                       325                330                335
Arg Val Tyr Lys Asn Gly Leu Tyr Asp Val Pro Arg Ile Leu Glu Asp
                   340                345                350
Ile Lys Ile Gly Lys Asn Ser Gly Glu Lys Leu Val Ala Val Leu Asn
                   355                360                365
```

<210> SEQ ID NO 9
<211> LENGTH: 12
<212> TYPE: PRT
<213> ORGANISM: Kluyveromyces lactis

<400> SEQUENCE: 9

```
Ser Tyr Gly Ala Asp Asp Val Phe Asp Tyr His Asp
 1               5                  10
```

-continued

<210> SEQ ID NO 10
<211> LENGTH: 12
<212> TYPE: PRT
<213> ORGANISM: Kluyveromyces lactis

<400> SEQUENCE: 10

Ile Gly Pro Glu Gly Ser Ile Leu Gly Cys Asp Ile
 1               5                  10

<210> SEQ ID NO 11
<211> LENGTH: 20
<212> TYPE: DNA
<213> ORGANISM: Artificial Sequence
<220> FEATURE:
<223> OTHER INFORMATION: Artificially synthesized primer sequence
<220> FEATURE:
<221> NAME/KEY: misc_feature
<222> LOCATION: 12
<223> OTHER INFORMATION: n = g, a, c or t

<400> SEQUENCE: 11
tgrtartcra anacrtcrtc                                                      20

<210> SEQ ID NO 12
<211> LENGTH: 20
<212> TYPE: DNA
<213> ORGANISM: Artificial Sequence
<220> FEATURE:
<223> OTHER INFORMATION: Artificially synthesized primer sequence
<220> FEATURE:
<221> NAME/KEY: misc_feature
<222> LOCATION: 18
<223> OTHER INFORMATION: n = g, a, c or t

<400> SEQUENCE: 12
atwgghccwg argghtcnat                                                      20

<210> SEQ ID NO 13
<211> LENGTH: 20
<212> TYPE: DNA
<213> ORGANISM: Artificial Sequence
<220> FEATURE:
<223> OTHER INFORMATION: Artificially synthesized primer sequence
<220> FEATURE:
<221> NAME/KEY: misc_feature
<222> LOCATION: 9
<223> OTHER INFORMATION: n = g, a, c or t

<400> SEQUENCE: 13
atwgghccng argghagyat                                                      20

<210> SEQ ID NO 14
<211> LENGTH: 509
<212> TYPE: DNA
<213> ORGANISM: Kluyveromyces lactis

<400> SEQUENCE: 14
attggtccwg argytcwat tctaggatgt gacattgctg gtacagttgt caaacttgga            60
ccaaatgcta gtactgactt gaaggttgga gataccggtt tcggttttgt tcacggtgct          120
tcccaaacag atcctaaaaa tggtgcattt gctgaatatg ccagggttta tccacctttg          180
ttttacaaga gtaacttaac tcactcaact gctgatgaaa tttctgaagg ccctgtgaag          240
aacttcgaat ctgctgcatc attgccagtt tcgttgacaa ctgctggtgt tagtttgtgt          300
catcacttgg gctcaaaaat ggaatggcac ccatctaccc cgcaacatac tcatccatta          360

```
ttgatttggg gtggtgctac agcagtgggt caacaactaa tccaagttgc caaacatatc    420
aatgcttata ctaagattgt aactgttgct tctaaaaagc atgaaaagct tttaaagtct    480
tatggtgctg atgacgtmtt cgactacca                                      509
```

```
<210> SEQ ID NO 15
<211> LENGTH: 30
<212> TYPE: DNA
<213> ORGANISM: Artificial Sequence
<220> FEATURE:
<223> OTHER INFORMATION: Artificially synthesized primer sequence

<400> SEQUENCE: 15
tccggtaccg acaactgtac cagcaatgtc                                     30
```

```
<210> SEQ ID NO 16
<211> LENGTH: 32
<212> TYPE: DNA
<213> ORGANISM: Artificial Sequence
<220> FEATURE:
<223> OTHER INFORMATION: Artificially synthesized primer sequence

<400> SEQUENCE: 16
atcggtacct atactaagat tgtaactgtt gc                                  32
```

```
<210> SEQ ID NO 17
<211> LENGTH: 21
<212> TYPE: DNA
<213> ORGANISM: Artificial Sequence
<220> FEATURE:
<223> OTHER INFORMATION: Artificially synthesized primer sequence

<400> SEQUENCE: 17
ccgggtaccc ttttagggtg a                                              21
```

```
<210> SEQ ID NO 18
<211> LENGTH: 23
<212> TYPE: DNA
<213> ORGANISM: Artificial Sequence
<220> FEATURE:
<223> OTHER INFORMATION: Artificially synthesized primer sequence

<400> SEQUENCE: 18
tcatgaagcc acagttaaat tcg                                            23
```

```
<210> SEQ ID NO 19
<211> LENGTH: 24
<212> TYPE: DNA
<213> ORGANISM: Artificial Sequence
<220> FEATURE:
<223> OTHER INFORMATION: Artificially synthesized primer sequence

<400> SEQUENCE: 19
atattcatat gatggatatc accg                                           24
```

```
<210> SEQ ID NO 20
<211> LENGTH: 41
<212> TYPE: DNA
<213> ORGANISM: Artificial Sequence
<220> FEATURE:
<223> OTHER INFORMATION: Artificially synthesized primer sequence

<400> SEQUENCE: 20
ctggaattct accatggctt cagttccaac cactcaaaaa g                        41
```

```
<210> SEQ ID NO 21
<211> LENGTH: 39
<212> TYPE: DNA
<213> ORGANISM: Artificial Sequence
<220> FEATURE:
<223> OTHER INFORMATION: Artificially synthesized primer sequence

<400> SEQUENCE: 21
gacaagcttc tagattataa cctggcaaca tacttaaca                              39

<210> SEQ ID NO 22
<211> LENGTH: 25
<212> TYPE: DNA
<213> ORGANISM: Artificial Sequence
<220> FEATURE:
<223> OTHER INFORMATION: Artificially synthesized primer sequence

<400> SEQUENCE: 22
caaacatgtc tgcctcgatt ccaga                                             25

<210> SEQ ID NO 23
<211> LENGTH: 31
<212> TYPE: DNA
<213> ORGANISM: Artificial Sequence
<220> FEATURE:
<223> OTHER INFORMATION: Artificially synthesized primer sequence

<400> SEQUENCE: 23
cagtctagat tatttcaaga cggcaaccaa c                                      31

<210> SEQ ID NO 24
<211> LENGTH: 32
<212> TYPE: DNA
<213> ORGANISM: Artificial Sequence
<220> FEATURE:
<223> OTHER INFORMATION: Artificially synthesized primer sequence

<400> SEQUENCE: 24
caaccatggc tcaagttgca attccagaaa cc                                     32

<210> SEQ ID NO 25
<211> LENGTH: 38
<212> TYPE: DNA
<213> ORGANISM: Artificial Sequence
<220> FEATURE:
<223> OTHER INFORMATION: Artificially synthesized primer sequence

<400> SEQUENCE: 25
gactctagat tagtttaata cggcaacgag tttttcac                               38

<210> SEQ ID NO 26
<211> LENGTH: 27
<212> TYPE: DNA
<213> ORGANISM: Artificial Sequence
<220> FEATURE:
<223> OTHER INFORMATION: Artificially synthesized primer sequence

<400> SEQUENCE: 26
gaaatcatga aagctgtcgt cattgaa                                           27

<210> SEQ ID NO 27
<211> LENGTH: 37
<212> TYPE: DNA
<213> ORGANISM: Artificial Sequence
<220> FEATURE:
<223> OTHER INFORMATION: Artificially synthesized primer sequence
```

-continued

```
<400> SEQUENCE: 27
gtttctagat tagtttaata cggcaackag tttttca                                37

<210> SEQ ID NO 28
<211> LENGTH: 18
<212> TYPE: DNA
<213> ORGANISM: Artificial Sequence
<220> FEATURE:
<223> OTHER INFORMATION: Artificially synthesized primer sequence

<400> SEQUENCE: 28
tgtaaaacga cggccagt                                                     18

<210> SEQ ID NO 29
<211> LENGTH: 18
<212> TYPE: DNA
<213> ORGANISM: Artificial Sequence
<220> FEATURE:
<223> OTHER INFORMATION: Artificially synthesized primer sequence

<400> SEQUENCE: 29
caggaaacag ctatgacc                                                     18
```